(12) United States Patent
Wibaux

(10) Patent No.: US 7,238,196 B2
(45) Date of Patent: Jul. 3, 2007

(54) SKIN-CONTACTING HEATABLE DRESSING

(75) Inventor: Anne Marie Paule Wibaux, Antwerp (BE)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/974,358

(22) Filed: Oct. 27, 2004

(65) Prior Publication Data

US 2005/0096574 A1 May 5, 2005

Related U.S. Application Data

(60) Provisional application No. 60/516,363, filed on Oct. 31, 2003.

(51) Int. Cl.
*A61F 7/02* (2006.01)
(52) U.S. Cl. .......................... 607/96; 607/98; 607/152
(58) Field of Classification Search .................. 607/96, 607/108, 149, 152, 153, 98; 219/544–545, 219/211; 252/502–503; 602/2, 41, 42, 48; 600/391, 394, 397; 214/549
See application file for complete search history.

(56) References Cited

U.S. PATENT DOCUMENTS

| | | | | |
|---|---|---|---|---|
| 3,687,143 A | * | 8/1972 | Schneeberger et al. ......... 602/2 |
| 4,226,247 A | * | 10/1980 | Hauser et al. .............. 600/391 |
| 4,518,851 A | * | 5/1985 | Oppitz ...................... 219/549 |
| 4,534,886 A | * | 8/1985 | Kraus et al. ................ 252/502 |
| 4,645,913 A | | 2/1987 | Oppitz ...................... 219/549 |
| 4,722,354 A | * | 2/1988 | Axelgaard et al. .......... 607/152 |
| 4,814,585 A | * | 3/1989 | Klein ......................... 219/545 |
| 4,817,594 A | | 4/1989 | Juhasz ......................... 602/42 |
| 4,846,176 A | | 7/1989 | Golden ...................... 607/104 |
| 5,643,480 A | * | 7/1997 | Gustavsson et al. ......... 219/211 |
| 5,662,624 A | | 9/1997 | Sundstrom et al. ......... 604/291 |
| 5,674,270 A | | 10/1997 | Viltro et al. ................. 607/112 |
| 5,913,849 A | | 6/1999 | Sundstrom et al. ......... 604/291 |
| 6,066,164 A | * | 5/2000 | Macher et al. ................ 607/96 |
| 6,172,344 B1 | | 1/2001 | Gordon et al. .............. 219/529 |
| 6,365,178 B1 | * | 4/2002 | Venkateshwaran et al. . 424/449 |
| 6,465,709 B1 | | 10/2002 | Sun et al. ...................... 602/48 |
| 6,468,295 B2 | * | 10/2002 | Augustine et al. ............ 607/96 |
| 6,483,990 B1 | | 11/2002 | Bikhovsky .................. 392/458 |
| 6,528,697 B1 | | 3/2003 | Knutson et al. ............... 602/54 |
| 6,585,670 B2 | | 7/2003 | Augustine et al. ............. 602/2 |
| 6,589,270 B2 | | 7/2003 | Augustine .................... 607/96 |

(Continued)

FOREIGN PATENT DOCUMENTS

DE   2 104 681   8/1972

(Continued)

*Primary Examiner*—Roy D. Gibson
(74) *Attorney, Agent, or Firm*—Renner, Otto, Boisselle & Sklar, LLP

(57) ABSTRACT

A skin-contacting heatable dressing including a pressure-sensitive adhesive layer having a first skin-contacting side and a second side; heat generating conductive carbon fibers contained within the skin-contacting pressure sensitive adhesive layer; and a source of electrical energy electrically connected to the carbon fibers. In one embodiment, the pressure-sensitive adhesive layer may include a transdermally absorbable medicament. In one embodiment, the dressing may include a backing layer. In one embodiment, the source of electrical energy may be a thin film battery, which may supplement or take the place of the backing layer.

39 Claims, 3 Drawing Sheets

U.S. PATENT DOCUMENTS

| | | |
|---|---|---|
| 6,605,051 B2 | 8/2003 | Augustine ........................ 602/2 |
| 6,861,570 B1* | 3/2005 | Flick ............................ 602/41 |
| 2003/0069529 A1 | 4/2003 | Augustine et al. ............. 602/48 |
| 2003/0109816 A1 | 6/2003 | Lachenbruch et al. ......... 602/2 |
| 2003/0144618 A1 | 7/2003 | Augustine ........................ 602/2 |
| 2003/0167029 A1 | 9/2003 | Augustine ..................... 602/42 |
| 2005/0043658 A1* | 2/2005 | Rix ................................ 602/2 |

FOREIGN PATENT DOCUMENTS

| | | |
|---|---|---|
| DE | 3637978 A1 | 5/1988 |
| EP | 0 278 139 B1 | 12/1991 |
| GB | 1 229 401 | 4/1971 |
| GB | 1 301 101 | 12/1972 |
| WO | WO 95/33358 | * 12/1995 |
| WO | 01/36010 A1 | 5/2001 |
| WO | 03/039417 A2 | 5/2003 |

* cited by examiner

← web direction →

SKIN-CONTACTING HEATABLE DRESSING

CROSS-REFERENCE TO RELATED APPLICATION

The present application is based on and claims priority under 35 U.S.C. §119(e)(1) to U.S. Provisional Application No. 60/516,363, filed 31 Oct. 2003, the disclosure of which is incorporated by reference herein in its entirety.

FIELD OF THE INVENTION

The present invention relates generally to dressings for use in wound care, burn care, post-surgical care and in similar applications, and more particularly to the field of heatable dressings for such use. The present invention further relates to heatable, thin, flexible devices which may be in direct contact with or be used close to mammalian skin.

BACKGROUND OF THE INVENTION

Heat treatment is widely used for promoting healing of wounds, burns, ulcers and post-surgically, for treatment of arthritis and muscle-source pain, and for promotion of healing generally. The normal human skin temperature is about 32° C.-33° C., which is a hypothermic temperature compared to normal core body temperature of about 37° C. The hypothermic condition of wounds inhibits healing. Studies have demonstrated that the local application of heat to hypothermic skin will result in some degree of vasodilation, which in turn results in an increase in local blood flow. Increased local blood flow in turn increases both the subcutaneous oxygen level and the availability of blood-borne healing factors, resulting in more collagen deposition and improved immune function. Studies have also demonstrated that temperatures much above the normal core body temperature of about 37° C. result in tissue damage and so do not contribute to promotion of wound therapy and healing.

Many currently available medical devices apply heat to wounds by use of infrared lamps, warm water pads, warm water bottles and by electrically heated pads. Treatment of wounds with infrared light requires that the wound be positioned under the light during therapy, necessitating patient immobility. Infrared light also can result in wounds drying, thereby slowing the healing process. Warm water pads and bottles and electrically heated pads powered by high voltage AC line electrical power transformed to low voltage all restrict patient mobility. In addition, electrically heated pads powered by high voltage AC line electrical power require use of a transformer to reduce voltage to a safe level, and even with such reduction the maintenance of an electrical connection to the high voltage electrical source constitutes a possible danger to patient safety.

A need continues to exist for heatable dressings which can provide a safe and effective level of heating to the skin of a mammalian subject, while being convenient, easy to use, and not restricting the mobility of the mammal to which the dressing is applied.

SUMMARY OF THE INVENTION

The present invention provides a skin-contacting heatable dressing which provides the benefits of applying safe and effective heat to the skin of a mammalian subject by means of an adhesive dressing which allows the subject to have a substantial degree of mobility and freedom of movement while the dressing is in place on the subject's body.

In one embodiment, the present invention relates to a skin-contacting heatable dressing including a pressure-sensitive adhesive layer having a first skin-contacting side and a second side; heat generating conductive fibers substantially embedded within the skin-contacting pressure sensitive adhesive layer; and a source of electrical energy electrically connected to the conductive fibers.

In one embodiment, the present invention relates to a skin-contacting heatable dressing including a pressure-sensitive adhesive layer having a first skin-contacting side and a second side; heat generating conductive fibers substantially embedded within the skin-contacting pressure sensitive adhesive layer; a backing layer over the second side of the pressure-sensitive adhesive layer; and a source of electrical energy electrically connected to the conductive fibers.

In one embodiment, the present invention relates to a skin-contacting heatable dressing including a pressure-sensitive adhesive layer having a first skin-contacting side and a second side, and containing one or more medicament capable of being transdermally absorbed; heat generating conductive fibers substantially embedded within the skin-contacting pressure sensitive adhesive layer; and a source of electrical energy electrically connected to the conductive fibers.

In one embodiment, the present invention relates to a method of making a skin-contacting heatable dressing including providing a substrate; applying a plurality of heat generating conductive fibers to the substrate; applying a pressure-sensitive adhesive layer over the plurality of heat generating conductive fibers and the substrate, wherein the heat generating conductive fibers are substantially embedded within the pressure sensitive adhesive layer; and electrically connecting a source of electrical energy to the conductive fibers.

Figure 1:
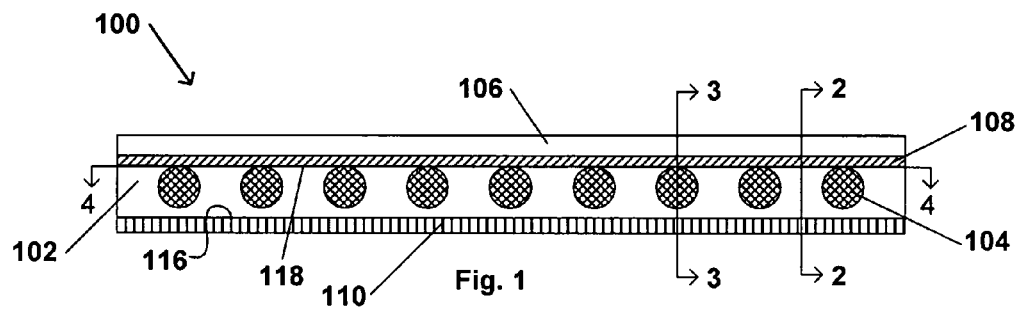
FIG. 1 is a schematic cross-sectional view of a skin-contacting heatable dressing in accordance with one embodiment of the invention.

It should be appreciated that for simplicity and clarity of illustration, elements shown in the Figures have not necessarily been drawn to scale. For example, in some Figures, the vertical dimensions of some of the elements may be exaggerated relative to horizontal dimensions for clarity. Further, where considered appropriate, reference numerals have been repeated among, or corresponding numbers have been used in, the Figures to indicate corresponding elements.

DETAILED DESCRIPTION

It should be appreciated that the process steps and structures described below do not form a complete process flow for manufacturing and using an end-product made by a process including the present invention. The present invention can be practiced in conjunction with fabrication techniques currently used in the art, and only so much of the commonly practiced process steps are included as are necessary for an understanding of the present invention.

In one embodiment, the present invention relates to a skin-contacting heatable dressing including a pressure-sensitive adhesive layer having a first skin-contacting side and a second side; heat generating conductive fibers substantially embedded within the skin-contacting pressure sensitive adhesive layer; and a source of electrical energy electrically connected to the conductive fibers. Thus, as described in more detail in the following, the present invention provides a skin-contacting heatable dressing which provides the benefits of applying safe and effective heat to the skin of a mammalian subject by means of an adhesive dressing which allows the subject to have a substantial degree of mobility and freedom of movement while the dressing is in place on the subject's body. In one embodiment, the pressure-sensitive adhesive contains a transdermally absorbable medicament. In one embodiment, the source of electrical energy is a thin film battery. In one embodiment, the dressing further includes a backing layer, and in another embodiment, the dressing further includes a release liner.

The following description of an embodiment of the invention is provided with reference to the drawings. The described embodiment is merely exemplary, and is not limiting of the scope of the invention, which is limited only to the full scope of the claims appended hereto.

Figures 2, 3:
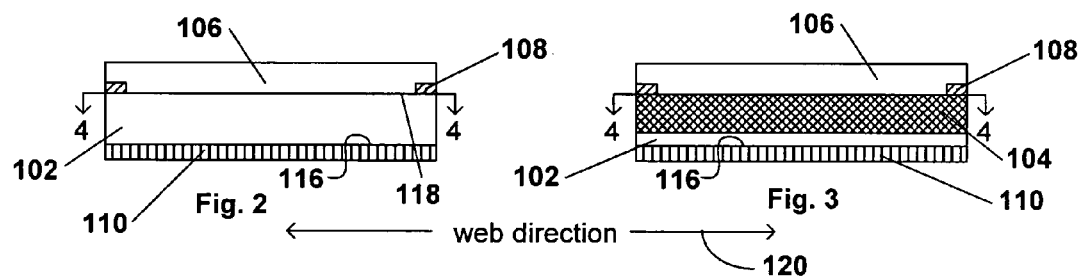
FIG. 2 is a schematic cross-sectional view of the skin-contacting heatable dressing of FIG. 1, taken at line 2-2 of FIG. 1.
FIG. 3 is a schematic cross-sectional view of the skin-contacting heatable dressing of FIG. 1, taken at line 3-3 of FIG. 1.
Figure 4:
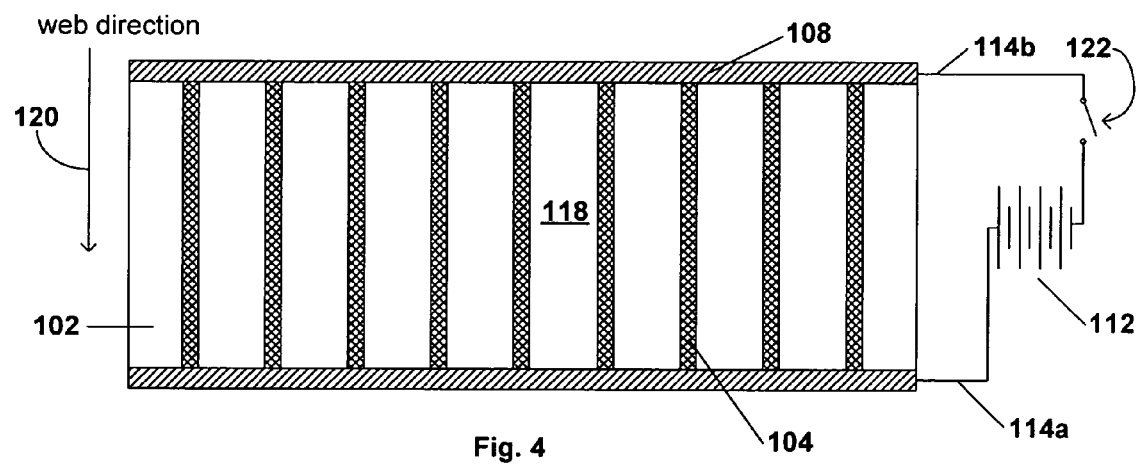
FIG. 4 is a schematic plan view of the skin-contacting heatable dressing of FIGS. 1-3, taken at line 4-4 of FIGS. 1 and 2.
Figure 5:
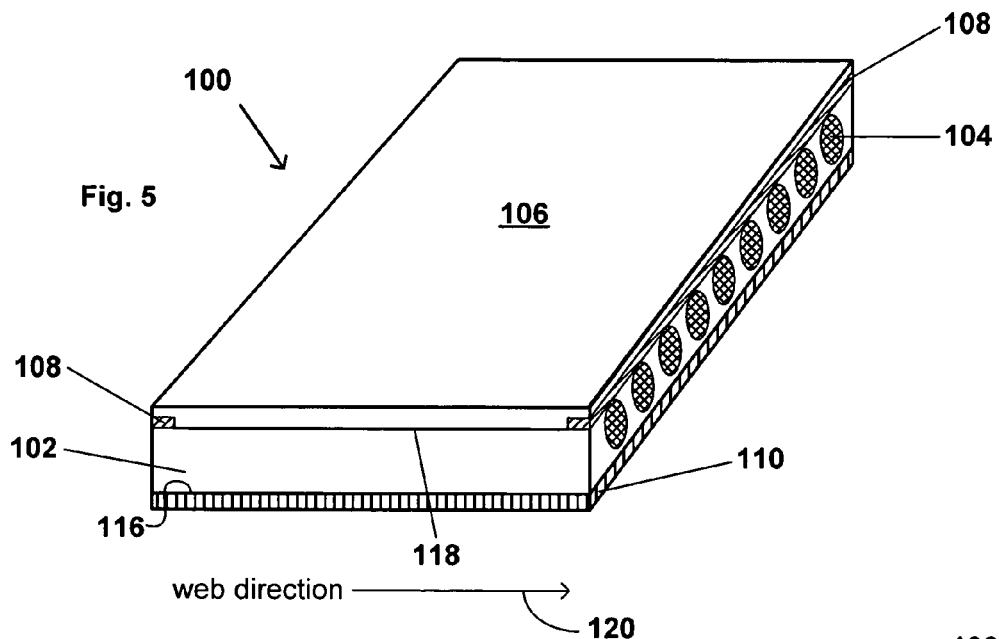
FIG. 5 is a perspective view of the skin-contacting heatable dressing of FIGS. 1-4.

FIG. 1 is a schematic cross-sectional view of a skin-contacting heatable dressing 100 in accordance with one embodiment of the invention. FIG. 2 is a schematic cross-sectional view of the skin-contacting heatable dressing 100 of FIG. 1, taken at line 2-2 of FIG. 1. FIG. 3 is a schematic cross-sectional view of the skin-contacting heatable dressing 100 of FIG. 1, similar to FIG. 2 except that it is taken at line 3-3 of FIG. 1. FIG. 4 is a schematic plan view of the skin-contacting heatable dressing 100 of FIGS. 1-3, taken at line 4-4 of FIGS. 1-3. FIG. 5 is a perspective view of the skin-contacting heatable dressing 100 of FIGS. 1-4.

Referring first to FIG. 1, the skin-contacting heatable dressing 100 shown includes a pressure-sensitive adhesive layer 102, conductive fibers 104 contained generally within the pressure-sensitive, an optional backing layer 106, conductive electrical leads 108, and a release liner 110. As shown in FIG. 4, a source of electrical energy, such as a battery 112, may be provided and electrically connected to the conductive fibers 104 by appropriate electrical leads 114a, 114b, such as wires or other conductive fibers.

The adhesive layer 102 has a skin-contacting surface 116 and an upper surface 118. Some or all of the skin-contacting surface 116 will be in contact with the skin of the mammal to which the dressing 100 is applied. The upper surface 118, in an embodiment in which the backing layer 106 is included, is in contact with the lower surface of the backing layer 106.

The conductive fibers 104 are described in more detail below. The conductive fibers 104 shown in FIGS. 1, 3 and 4 are greatly exaggerated in thickness and greatly reduced in number, for ease of illustration. In an actual dressing 100, there may be hundreds or thousands of conductive fibers 104, and the diameter of the fibers are much smaller, in comparison to the thickness of the pressure-sensitive adhesive layer 102, than as shown in FIGS. 1, 3 and 4. For these reasons, it would be practically difficult to obtain a straight-line cross-sectional view devoid of conductive fibers 104 such as the schematic illustration of FIG. 2.

In one embodiment, the conductive fibers 104 are arranged in generally parallel arrangement with respect to one another, while including a substantial amount of intertwining, intermingling, crossing and generally being in contact with one another. As will be understood, in actuality the conductive fibers 104 are not likely to be arranged in neatly parallel rows as schematically depicted in, e.g., FIG. 4. In one embodiment, the conductive fibers 104 are in approximately, generally parallel arrangement. In another embodiment, the conductive fibers 104 are intertwined and contact each other so that substantially all of the conductive fibers conduct electricity and thereby generate heat along at least a portion of the fiber length. In another embodiment, the conductive fibers 104 are in the form of a woven or non-woven fabric, in which the individual conductive fibers are in contact with a large number of other conductive fibers. In one embodiment, the present invention may include any of the foregoing arrangements of conductive fibers 104, or any other arrangement which may be known in the art.

In FIG. 1, the web direction is actually perpendicular to and into the plane of the paper. In FIGS. 2-4, the web direction is indicated by an arrow 120. The conductive fibers 104, in one embodiment, as best shown in FIGS. 1 and 4, are distributed generally parallel to, in or along the web direction (indicated by the arrow 120) of the dressing 100, and the conductive electrical leads 108 are arranged generally perpendicular to or across the web direction. In another embodiment, the conductive fibers 104 may be oriented generally perpendicular to or across the web direction, while the conductive electrical leads 108 may be oriented generally parallel to, in or along the web direction. The respective directions of the conductive fibers 104 and the conductive electrical leads 108 can be suitably selected based on factors known to those of skill in the art, for example, manufacturing and dressing stability, flexibility and dispensability considerations.

The backing layer 106 is optional. However, in most cases, it is convenient to include the backing layer 106, since the pressure-sensitive adhesive layer 102 is sticky, and having the upper surface 118 exposed would result in dirt and other environmental materials becoming adhered to the upper surface 118 of the pressure-sensitive adhesive layer 102. In one embodiment, the backing layer 106 is formed by adding materials to the upper portions of the pressure-sensitive adhesive layer 102 to reduce its tack. Such materials may include, for example, talc or other known anti-blocking agents.

As shown in FIGS. 1-3, the conductive electrical leads 108 may be applied along opposite side edges of the dressing 100. The conductive electrical leads 108 are in contact with a substantial number of the conductive fibers 104. Since the conductive fibers 104 are distributed throughout the pressure-sensitive adhesive layer 102, not all of the conductive fibers will be directly in contact with the conductive electrical leads 108. However, as a result of the overlapping, intertwined distribution of the conductive fibers 108, in one embodiment, substantially all of the conductive fibers will conduct at least some electrical current at some point along their length.

As shown in FIG. 4, in one embodiment, the source of electrical energy 112, may be connected to the conductive electrical leads 108 via the electrical lead wires 114a, 114b, and may include a switch 122. In one embodiment, the switch 122 is a simple two position (on-off) switch. In one embodiment, the switch is a multiple-position switch including resistors, having a plurality of positions for providing a plurality of electrical currents or power levels to the dressing 100. Such switches are well known in the art, and need not be described in detail. In one embodiment, the dressing 100 is free of a thermostatic control operating by sensing temperature directly or indirectly. In one embodiment, the temperature of the dressing 100 is manually controlled by the user. In one embodiment, the manual control by the user includes only use of an on-off switch, with power being applied to the dressing on an as-needed basis. In another embodiment, the manual control by the user includes use of a multi-level switch, in which the user can select from a plurality of power levels to be applied to the dressing 100, thus allowing selection of a comfortable or desirable temperature of the dressing 100.

In one embodiment, the dressing 100 includes a quantity and/or quality of conductive fibers such that when a selected energy source is applied, the dressing reaches a temperature in the range from about 25° C. to about 40° C., and in another embodiment, the temperature is maintained in the range from about 37° C. to about 38.5° C. In one embodiment, the dressing reaches a temperature in the range from normal skin temperature (i.e., about 32° C.) to about 39° C.

In one embodiment, for a given input of voltage, power or current, the quantity and/or quality of the conductive fibers 104 can be selected to obtain a predetermined temperature in the desired range. This results from the well known relationship, expressed as Ohm's Law, between current I, voltage V, and resistance R, I=V/R, or rearranged, R=V/I. Thus, selection of an appropriate quantity of an appropriate quality of conductive fibers 104 would allow a user to predetermine the temperature which the dressing 100 would attain, given a particular voltage input.

The resistance (R) of a material depends on its length L, cross-sectional area A, and the resistivity (the Greek letter rho, ρ), a number that depends on the material:

$R = \rho L/A$

Using this equation, it is clear that by selection of the material and the length and diameter or cross-sectional area of the conductive fibers, a selected resistance can be obtained. As is well known, the resistance R is related to the wattage or power P and applied voltage V, $P = V^2/R$ and therefore the heat generated by the dressing can be controlled and adjusted by selection of the appropriate conductive fibers.

The numerical limits of the ranges and ratios disclosed herein may be combined, the disclosed ranges are intended to include all intermediate values, and sub-ranges may be selected from the disclosed ranges as needed. For example, in the foregoing temperature ranges, although a range from about 25° C. to about 39° C. is not specifically recited, it is considered to be within the scope of the disclosure. Similarly, although a temperature of 38° C. is not specifically recited, it is within the disclosed range and so is considered to be within the scope of the disclosure.

Figure 9:
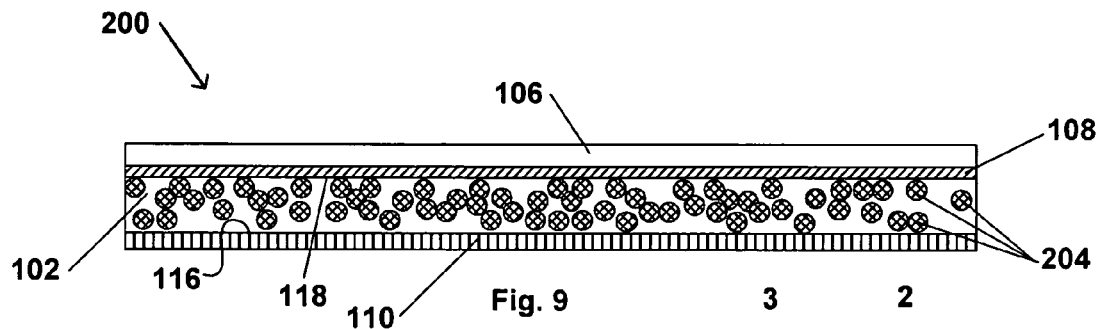
FIG. 9 is a schematic cross-sectional view of a skin-contacting heatable dressing in accordance with another embodiment of the invention.

FIG. 9 is a schematic cross-sectional view of a skin-contacting heatable dressing 200 in accordance with another embodiment of the invention. FIG. 9 schematically depicts an embodiment of the present invention similar to that shown in FIG. 1, except that the conductive fibers 204 are smaller in diameter, relative to the other portions of the dressing, and more numerous than the conductive fibers 104 shown in FIG. 1. As schematically illustrated in FIG. 9, in some embodiments of the present invention, the conductive fibers are in contact with each other, and may also overlap, cross and generally intermingle with one another across the heatable dressing 200.

Pressure-Sensitive Adhesives

Any pressure-sensitive adhesive that is capable of adhering to mammalian skin and is free of ingredients known to cause undue irritation or toxicity to mammals can be utilized in the heatable dressings of the present invention. For example, the pressure sensitive adhesive may include one or more of a silicone pressure sensitive adhesive, rubber pressure sensitive adhesive, acrylic pressure sensitive adhesive, a hydrogel pressure sensitive adhesive or other known pressure-sensitive adhesives. A description of useful pressure-sensitive adhesives may be found in *Encyclopedia of Polymer Science and Engineering*, Vol. 13. Wiley-Interscience Publishers (New York, 1988). Additional description of useful pressure-sensitive adhesives may be found in *Encyclopedia of Polymer Science and Technology*, Vol. 1, Interscience Publishers (New York, 1964).

In general, the pressure-sensitive adhesives used herein may be any of the pressure-sensitive adhesives described in the above references. In one embodiment of the invention, pressure-sensitive adhesives comprise natural or synthetic elastomers, or acrylic-based adhesives. Two or more pressure-sensitive adhesive layers may be used in the dressing and may be of the same composition or they may be different so long as the adhesive layers have sufficient tack to adhere to each other, to the backing, and optionally to a release liner.

The pressure-sensitive adhesives in each adhesive layer of the present invention can be acrylic based such as those taught in U.S. Pat. No. 5,164,444 (Bernard, acrylic emulsion), U.S. Pat. No. 5,623,011 (Bernard, tackified acrylic emulsion) and U.S. Pat. No. 6,306,982 (Lee et al., general purpose inherently tacky acrylic pressure sensitive adhesives. The adhesive can also be rubber-based such as those taught in U.S. Pat. No. 5,705,551 (Sasaki et al, rubber hot melt). It can also be radiation curable mixture of monomers with initiators and other ingredients such as those taught in U.S. Pat. No. 5,232,958 (Ang, UV cured acrylic) and U.S. Pat. No. 5,232,958 (Mallya et al, EB cured). The disclosures of these patents as they relate to acrylic adhesives are hereby incorporated by reference. Although the pressure-sensitive adhesives in some of the examples of the present application are emulsion and hot melt pressure-sensitive adhesives, other forms such as solvent adhesives may be used since the same physical principles apply.

Commercially available pressure-sensitive adhesives are useful in the invention. Examples of these adhesives include the hot melt pressure-sensitive adhesives available from H.B. Fuller Company, St. Paul, Minn. as HM-1597, HL-2207-X, HL-2115-X, HL-2193-X. Other useful commercially available pressure-sensitive adhesives include those available from Century Adhesives Corporation, Columbus, Ohio. Another useful acrylic pressure-sensitive adhesive comprises a blend of emulsion polymer particles with dispersion tackifier particles as generally described in Example 2 of U.S. Pat. No. 6,306,982, to Lee et al. The polymer is made by emulsion polymerization of 2-ethylhexyl acrylate, vinyl acetate, dioctyl maleate, acrylic and methacrylic comonomers as described in U.S. Pat. No. 5,164,444 by M. Bernard, resulting in the latex particle size of about 0.2 microns in weight average diameters and a gel content of about 60%.

Conventional pressure-sensitive adhesives, including silicone-based pressure-sensitive adhesives, rubber-based pressure-sensitive adhesives, and acrylic-based pressure-sensitive adhesives are useful. A commercial example of a hot melt adhesive is H2187-01, sold by Ato Findley, Inc., of Wauwatusa, Wis. In addition, rubber based block copolymer pressure-sensitive adhesives described in U.S. Pat. No. 3,239,478 (Harlan) also can be utilized in the adhesive constructions of the present invention, and this patent is hereby incorporated by a reference for its disclosure of such hot melt adhesives.

In one embodiment, the skin-contacting pressure-sensitive adhesive layer may be formed from an acrylic based polymer. It is contemplated that any acrylic based polymer capable of forming an adhesive layer with sufficient tack to adhere to the backing layer, the release liner and to mammalian skin may function in the present invention. In certain embodiments, the acrylic polymers for the pressure-sensitive adhesive layers include those formed from polymerization of at least one alkyl acrylate monomer containing from about 4 to about 12 carbon atoms in the alkyl group, and present in an amount from about 35-95% by weight of the polymer or copolymer, as disclosed in U.S. Pat. No. 5,264,532 issued to Barnard. Optionally, the acrylic based pressure-sensitive adhesive might be formed from a single polymeric species.

Advantageously, the glass transition temperature of a pressure-sensitive adhesive layer comprising acrylic polymers can be varied by adjusting the amount of polar, or "hard monomers", in the copolymer, as taught by U.S. Pat. No. 5,264,532, incorporated herein by reference. The greater the percentage by weight of hard monomers is an acrylic copolymer, the higher the glass transition temperature. Hard monomers contemplated useful for the present invention include vinyl esters, carboxylic acids, and methacrylates, in concentrations by weight ranging from about zero to about thirty-five percent by weight of the polymer.

In another embodiment, the pressure-sensitive adhesive utilized in the present invention may comprise rubber based elastomer materials containing useful rubber based elastomer materials include linear, branched, grafted, or radial block copolymers represented by the diblock structure A-B, the triblock A-B-A, the radial or coupled structures (A-B)$_n$, and combinations of these where A represents a hard thermoplastic phase or block which is non-rubbery or glassy or crystalline at room temperature but fluid at higher temperatures, and B represents a soft block which is rubbery or elastomeric at service or room temperature. These thermoplastic elastomers may comprise from about 75% to about 95% by weight of rubbery segments and from about 5% to about 25% by weight of non-rubbery segments.

The non-rubbery segments or hard blocks comprise polymers of mono- and polycyclic aromatic hydrocarbons, and more particularly vinyl-substituted aromatic hydrocarbons which may be monocyclic or bicyclic in nature. The preferred rubbery blocks or segments are polymer blocks of homopolymers or copolymers of aliphatic conjugated dienes. Rubbery materials such as polyisoprene, polybutadiene, and styrene butadiene rubbers may be used to form the rubbery block or segment. Particularly preferred rubbery segments include polydienes and saturated olefin rubbers of ethylene/butylene or ethylene/propylene copolymers. The latter rubbers may be obtained from the corresponding unsaturated polyalkylene moieties such as polybutadiene and polyisoprene by hydrogenation thereof.

The block copolymers of vinyl aromatic hydrocarbons and conjugated dienes which may be utilized include any of those which exhibit elastomeric properties. The block copolymers may be diblock, triblock, multiblock, starblock, polyblock or graftblock copolymers. Throughout this specification and claims, the terms diblock, triblock, multiblock, polyblock, and graft or grafted-block with respect to the structural features of block copolymers are to be given their normal meaning as defined in the literature such as in the *Encyclopedia of Polymer Science and Engineering*, Vol. 2, (1985) John Wiley & Sons, Inc., New York, pp. 325-326, and by J. E. McGrath in *Block Copolymers, Science Technology*, Dale J. Meier, Ed., Harwood Academic Publishers, 1979, at pages 1-5.

Such block copolymers may contain various ratios of conjugated dienes to vinyl aromatic hydrocarbons including those containing up to about 40% by weight of vinyl aromatic hydrocarbon. Accordingly, multi-block copolymers may be utilized which are linear or radial symmetric or asymmetric and which have structures represented by the formulae A-B, A-B-A, A-B-A-B, B-A-B, (AB)$_{0,1,2}$ . . . BA, etc., wherein A is a polymer block of a vinyl aromatic hydrocarbon or a conjugated diene/vinyl aromatic hydrocarbon tapered copolymer block, and B is a rubbery polymer block of a conjugated diene.

The block copolymers may be prepared by any of the well-known block polymerization or copolymerization procedures including sequential addition of monomer, incremental addition of monomer, or coupling techniques as illustrated in, for example, U.S. Pat. Nos. 3,251,905; 3,390,207; 3,598,887; and 4,219,627. As well known, tapered copolymer blocks can be incorporated in the multi-block copolymers by copolymerizing a mixture of conjugated diene and vinyl aromatic hydrocarbon monomers utilizing the difference in their copolymerization reactivity rates. Various patents describe the preparation of multi-block copolymers containing tapered copolymer blocks including U.S. Pat. Nos. 3,251,905; 3,639,521; and 4,208,356, the disclosures of which are hereby incorporated by reference.

Conjugated dienes which may be utilized to prepare the polymers and copolymers are those containing from 4 to about 10 carbon atoms and more generally, from 4 to 6 carbon atoms. Examples include from 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used. The preferred conjugated dienes are isoprene and 1,3-butadiene.

Examples of vinyl aromatic hydrocarbons which may be utilized to prepare the copolymers include styrene and the various substituted styrenes such as o-methylstyrene, p-methylstyrene, p-tert-butylstyrene, 1,3-dimethylstyrene, alpha-methylstyrene, beta-methylstyrene, p-isopropylstyrene, 2,3-dimethylstyrene, o-chlorostyrene, p-chlorostyrene, o-bromostyrene, 2-chloro-4-methylstyrene, etc. The preferred vinyl aromatic hydrocarbon is styrene.

Many of the above-described copolymers of conjugated dienes and vinyl aromatic compounds are commercially available. The number average molecular weight of the block copolymers, prior to hydrogenation, is from about 20,000 to about 500,000, preferably from about 40,000 to about 300,000.

The average molecular weights of the individual blocks within the copolymers may vary within certain limits. In most instances, the vinyl aromatic block will have a number average molecular weight in the order of about 2000 to about 125,000, and preferably between about 4000 and 60,000. The conjugated diene blocks either before or after hydrogenation will have number average molecular weights in the order of about 10,000 to about 450,000 and more preferably from about 35,000 to 150,000.

Also, prior to hydrogenation, the vinyl content of the conjugated diene portion generally is from about 10% to about 80%, and the vinyl content is preferably from about 25% to about 65%, particularly 35% to 55% when it is desired that the modified block copolymer exhibit rubbery elasticity. The vinyl content of the block copolymer can be measured by means of nuclear magnetic resonance.

Specific examples of diblock copolymers include styrene-butadiene (SB), styrene-isoprene (SI), and the hydrogenated derivatives thereof. Examples of triblock polymers include styrene-butadiene-styrene (SBS), styrene-isoprene-styrene (SIS), alpha-methylstyrene-butadiene-alpha-methylstyrene, and alpha-methylstyrene-isoprene alpha-methylstyrene. Examples of commercially available block copolymers useful as the adhesives in the present invention include those available from Shell Chemical Company and listed in the following Table I.

TABLE I

| Kraton | Type | Styrene/Rubber Ratio (w) | Melt Index |
|---|---|---|---|
| D1101 | Linear SBS | 31/69 | <1 |
| D1107P | Linear SIS | 15/85 | 11 |
| D1111 | Linear SIS | 22/78 | 3 |
| D1112P | Linear SIS | 15/85 | 23 |
| D1113P | Linear SIS | 16/84 | 24 |
| D1117P | Linear SIS | 17/83 | 33 |
| D1320X | Multi-arm (SI)$_n$ | 10/90 | NA |

Vector 4111 is a SIS block copolymer available from Dexco of Houston, Tex.

Upon hydrogenation of the SBS copolymers comprising a rubbery segment of a mixture of 1,4 and 1,2 isomers, a styrene-ethylene-butylene styrene (SEBS) block copolymer is obtained. Similarly, hydrogenation of an SIS polymer yields a styrene-ethylene propylene-styrene (SEPS) block copolymer.

The selective hydrogenation of the block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference. Such hydrogenation of the block copolymers which are carried out in a manner and to extent as to produce selectively hydrogenated copolymers having a residual unsaturation content in the polydiene block of from about 0.5% to about 20% of their original unsaturation content prior to hydrogenation.

In one embodiment, the conjugated diene portion of the block copolymer is at least 90% saturated and more often at least 95% saturated while the vinyl aromatic portion is not significantly hydrogenated. Particularly useful hydrogenated block copolymers are hydrogenated products of the block copolymers of styrene-isoprene-styrene such as a styrene-(ethylene/propylene)-styrene block polymer. When a polystyrene-polybutadiene-polystyrene block copolymer is hydrogenated, it is desirable that the 1,2-polybutadiene to 1,4-polybutadiene ratio in the polymer is from about 30:70 to about 70:30. When such a block copolymer is hydrogenated, the resulting product resembles a regular copolymer block of ethylene and 1-butene (EB). As noted above, when the conjugated diene employed as isoprene, the resulting hydrogenated product resembles a regular copolymer block of ethylene and propylene (EP).

A number of selectively hydrogenated block copolymers are available commercially from Shell Chemical Company under the general trade designation "Kraton G." One example is Kraton G1652 which is a hydrogenated SBS triblock comprising about 30% by weight of styrene end blocks and a midblock which is a copolymer of ethylene and 1-butene (EB). A lower molecular weight version of G1652 is available from Shell under the designation Kraton G1650. Kraton G1651 is another SEBS block copolymer which contains about 33% by weight of styrene. Kraton G1657 is an SEBS diblock copolymer which contains about 13% w styrene. This styrene content is lower than the styrene content in Kraton G1650 and Kraton G1652.

In another embodiment, the selectively hydrogenated block copolymer is of the formula $$B_n(AB)_oA_p$$

wherein
n=0 or 1;
o is 1 to 100;
p is 0 or 1;
each B prior to hydrogenation is predominantly a polymerized conjugated diene hydrocarbon block having a number average molecular weight of about 20,000 to about 450,000;
each A is predominantly a polymerized vinyl aromatic hydrocarbon block having a number average molecular weight of from about 2000 to about 115,000; the blocks of A constituting about 5% to about 95% by weight of the copolymer; and the unsaturation of the block B is less than about 10% of the original unsaturation. In other embodiments, the unsaturation of block B is reduced upon hydrogenation to less than 5% of its original value, and the average unsaturation of the hydrogenated block copolymer is reduced to less than 20% of its original value.

The block copolymers may also include functionalized polymers such as may be obtained by reacting an alpha, beta-olefinically unsaturated monocarboxylic or dicarboxylic acid reagent onto selectively hydrogenated block copolymers of vinyl aromatic hydrocarbons and conjugated dienes as described above. The reaction between the carboxylic acid reagent in the graft block copolymer can be effected in solutions or by a melt process in the presence of a free radical initiator.

The preparation of various selectively hydrogenated block copolymers of conjugated dienes and vinyl aromatic hydrocarbons which have been grafted with a carboxylic acid reagent is described in a number of patents including U.S. Pat. Nos. 4,578,429; 4,657,970; and 4,795,782, and the disclosures of these patents relating to grafted selectively hydrogenated block copolymers of conjugated dienes and vinyl aromatic compounds, and the preparation of such compounds are hereby incorporated by reference. U.S. Pat. No. 4,795,782 describes and gives examples of the preparation of the grafted block copolymers by the solution process and the melt process. U.S. Pat. No. 4,578,429 contains an example of grafting of Kraton G1652 (SEBS) polymer with maleic an hydride with 2,5-dimethyl-2,5-di(t-butylperoxy) hexane by a melt reaction in a twin screw extruder. (See Col. 8, lines 40-61.)

Examples of commercially available maleated selectively hydrogenated copolymers of styrene and butadiene include Kraton FG1901X, FG1921X, and FG1924X from Shell, often referred to as maleated selectively hydrogenated SEBS copolymers. FG1901X contains about 1.7% w bound functionality as succinic anhydride and about 28% w of styrene. FG1921X contains about 1% w of bound functionality as succinic anhydride and 29% w of styrene. FG1924X contains about 13% styrene and about 1% bound functionality as succinic anhydride.

Useful block copolymers also are available from Nippon Zeon Co., 2-1, Marunochi, Chiyoda-ku, Tokyo, Japan. For example, Quintac 3530 is available from Nippon Zeon and is believed to be a linear styrene-isoprene-styrene block copolymer.

Unsaturated elastomeric polymers and other polymers and copolymers which are not inherently tacky can be rendered tacky when compounded with an external tackifier. Tackifiers, are generally hydrocarbon resins, wood resins, rosins, rosin derivatives, and the like, which when present in concentrations ranging from about 40% to about 90% by weight of the total adhesive composition, more preferably from about 45% to about 85% by weight, impart pressure-sensitive adhesive characteristics to the elastomeric polymer adhesive formulation. Compositions containing less than about 40% by weight of tackifier additive do not generally show sufficient "quickstick," or initial adhesion, to function as a pressure-sensitive adhesive, and therefore are not inherently tacky. Compositions with too high a concentration of tackifying additive, on the other hand, generally show too little cohesive strength to work properly in most intended use applications of constructions made in accordance with the instant invention.

It is contemplated that any tackifier known by those of skill in the art to be compatible with elastomeric polymer compositions may be used with the present embodiment of the invention. One such tackifier, found useful is Wingtak 10, a synthetic polyterpene resin which is liquid at room temperature, and sold by the Goodyear Tire and Rubber Company of Akron, Ohio. Wingtak 95 is a synthetic tackifier resin also available from Goodyear which comprises predominantly a polymer derived from piperylene and isoprene. Other suitable tackifying additives may include Escorez 1310, an aliphatic hydrocarbon resin, and Escorez 2596, a $C_5$-$C_9$ (aromatic modified aliphatic) resin, both manufactured by Exxon of Irving, Tex. Of course, as can be appreciated by those of skill in the art, a variety of different tackifying additives may be used to practice the present invention.

In addition to the tackifiers, other additives may be included in the pressure-sensitive adhesives to impart desired properties. For example, plasticizers may be included, and they are known to decrease the glass transition temperature of an adhesive composition containing elastomeric polymers. An example of a useful plasticizer is Shellflex 371, a naphthenic processing oil available from Shell Oil Company of Houston, Tex. Antioxidants also may be included on the adhesive compositions. Suitable antioxidants include Irgafos 168 and Irganox 565 available from Ciba-Geigy, Hawthorne, N.Y. Cutting agents such as waxes and surfactants also may be included in the adhesives.

Hydrogel Pressure-Sensitive Adhesives

In another embodiment, the pressure-sensitive adhesive may comprise a hydrogel or hydrocolloid pressure-sensitive adhesive. In one embodiment, the hydrogel or hydrocolloid pressure-sensitive adhesive may comprise any of these materials disclosed in copending U.S. Provisional Patent Application No. 60/472,273, filed 20 May 2003, entitled MULTI-DRESSING SYSTEM FOR MANAGING SKIN WOUNDS, which is incorporated herein by reference for its teachings relating to pressure-sensitive adhesives and particularly for its teachings relating to hydrogel or hydrocolloid pressure-sensitive adhesives. For convenience, the hydrogel or hydrocolloid pressure-sensitive adhesives are referred to herein after simply as hydrogel pressure-sensitive adhesives.

In one embodiment of the present invention, the hydrogel pressure-sensitive adhesive comprises a water soluble polymer such as cellulose. In one embodiment, the hydrogel pressure-sensitive adhesive comprises an aqueous mixture of a radiation crosslinkable water-soluble polymer such as a polymer of N-vinyl-2-pyrrolidone and ethylene oxide and a humectant such as propylene glycol. In one embodiment, the hydrogel pressure-sensitive adhesive comprises polyvinyl pyrrolidone and polyvinyl alcohol, a polar plasticizer or humectant such as propylene glycol and water. The hydrogel pressure-sensitive adhesive may also contain cellulose derivatives to increase strength and guar gum to increase tackiness. In one embodiment, the hydrogel pressure-sensitive adhesive comprises a water-absorbent resin such as a vinyl acetate-acrylic acid ester copolymer that swells to form a hydrogel upon contact with water. In this embodiment, the adhesive may comprise a gelling agent, where the gelling agent comprises, for example, methylcellulose, a natural gum, glucose, propylparben, methylparaben, and sodium chloride. In other embodiments, the pressure-sensitive adhesive hydrogels of the present invention may further comprise a substituted urea of the formula R—NH—CO—$NH_2$, wherein R is hydrogen, hydroxyl, or a lower alkyl having from 1 to 8 carbon atoms selected from the group consisting of methyl, ethyl, propyl, isopropyl, butyl, isobutyl, tert-butyl, pentyl, hexyl, heptyl and octyl. In one embodiment, the substituted urea is butylurea.

The hydrogels of the present invention may further comprise coloring, fragrance or other pharmaceutically acceptable additives.

In one embodiment, the heatable dressings include a fluid-absorbing hydrogel pressure-sensitive adhesive material, which provides both adhesion to the patient in the vicinity of the wound and absorbent capability for wound exudate which may be produced by a wound in the early stages of healing. In one embodiment, the fluid-absorbing pressure-sensitive adhesive includes a mixture of an adhesive material and at least one water-soluble and/or water-swellable polymer. The water-soluble and/or water-swellable polymer provides the fluid-absorbing capability of the pressure-sensitive adhesive in the dressing.

In one embodiment, the fluid-absorbing hydrogel pressure-sensitive adhesive material includes one or more solid, physically cross-linked thermoplastic elastomer components such as styrene-olefin-styrene copolymers and a liquid rubber component which, in some embodiments, is substantially resin free. The adhesive material provides "dry tack" to adhere the adhesive to dry, i.e., not moist, skin. Dispersed within adhesive material is a fluid-absorbing material such as an absorbent polymer. Useful as the absorbent polymer are, for example, insoluble calcium alginate and synthetic insoluble absorbents such as crystalline sodium carboxymethyl cellulose. In another embodiment, water-soluble hydrocolloids may also be used for this fluid-absorbing material.

In addition to the fluid-absorbing pressure-sensitive adhesive, in one embodiment, the dressings also include an occlusive top layer of a film material, such as a polymeric film. The occlusive top layer may be the backing layer of the dressing, as described herein. The film may be a continuous web or may be a non-woven fibrous web. In one embodiment, the occlusive top layer provides an occlusive function to the heatable dressing. The occlusive top layer may provide a selected or controlled degree of moisture transmission.

In one embodiment, the adhesive material and the at least one water-soluble and/or water-swellable absorbent polymer, of which the fluid-absorbing hydrogel pressure-sensitive adhesive is comprised, are present as a continuous phase comprising the adhesive material and, dispersed within the continuous phase, a discontinuous phase comprising the at least one water-soluble and/or water-swellable absorbent polymer.

Adhesive Material of Hydrogel Pressure-Sensitive Adhesive

The adhesive material of the fluid-absorbing hydrogel pressure-sensitive adhesive of the dressings of the present invention may include a variety of pressure-sensitive adhesive materials known in the art. In one embodiment, the adhesive may include any medical grade adhesive. In one embodiment, the medical adhesives include suitable acrylic based pressure sensitive adhesives (PSAs), suitable rubber-based pressure sensitive adhesives and suitable silicone pressure sensitive adhesives. In one embodiment, the pressure-sensitive adhesive portion may comprise any of the pressure-sensitive adhesive materials disclosed herein for use in the pressure-sensitive adhesive layer.

Useful rubber-based pressure-sensitive adhesives include those taught in U.S. Pat. No. 5,705,551 (Sasaki et al.) and in U.S. Pat. No. 4,080,348 (Korpman), the disclosures of which are hereby incorporated by reference. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

In one embodiment, a particularly useful rubber-based adhesive is that which has a thermoplastic elastomeric component and a resin component. The thermoplastic elastomeric component contains about 55-85 parts of a simple A-B block copolymer wherein the A-blocks are derived from styrene homologs and the B-blocks are derived from isoprene, and about 15-45 parts of a linear or radical A-B-A block copolymer wherein the A-blocks are derived from styrene or styrene homologs and the B-blocks are derived from conjugated dienes or lower alkenes, the A-blocks in the A-B block copolymer constituting about 10-18 percent by weight of the A-B copolymer and the total A-B and A-B-A copolymers containing about 20 percent or less styrene.

In one embodiment, the resin component comprises a tackifier resin for the elastomeric component. In general any compatible conventional tackifier resin or mixture of such resins may be used. These include hydrocarbon resins, rosin and rosin derivatives, polyterpenes and other tackifiers. The adhesive composition contains about 20-300 parts of the resin component per one hundred parts by weight of the thermoplastic elastomeric component. One such rubber-based adhesive is commercially available from Ato Findley under the trade name HM3210.

Useful acrylic based pressure-sensitive adhesives include those taught in U.S. Pat. No. 5,947,917 (Carte), and U.S. Pat. No. 5,164,444 (Bernard, acrylic emulsion), U.S. Pat. No. 5,623,011 (Bernard, tackified acrylic emulsion). The acrylic pressure-sensitive adhesive may also be a radiation curable mixture of monomers with initiators and other ingredients such as those taught in U.S. Pat. No. 5,232,958 (Ang, UV cured acrylic) and U.S. Pat. No. 5,232,958 (Mallya et al, EB cured). The disclosures of these patents as they relate to acrylic adhesives are hereby incorporated by reference.

In one embodiment, the adhesive material may include solid rubbers such as linear or radial A-B-A block copolymers or mixtures of these A-B-A block copolymers with simple A-B block copolymers. However, the proportion of A-B block copolymers, relative to the A-B-A block copolymers, should not normally exceed 85% by weight of the (total) block copolymers. In one embodiment, the proportion is in the range from about 35 to about 85% by weight of the block copolymers, and in another embodiment, the proportion is from about 55 to about 75% by weight of the block copolymers. In one embodiment, lower amounts such as 10 to 35% by weight of the block copolymers are used. These block copolymers can be based on styrene-butadiene, styrene-isoprene, and hydrogenated styrene-diene copolymers such as styrene ethylene-butylene. Suitable styrene-diene copolymers are exemplified by a blend of linear styrene-isoprene-styrene triblock copolymer and linear styrene-isoprene diblock copolymer. Such a material is available from Kraton Polymers as KRATON® D-1161 K and has a bound styrene content of about 15% and a diblock content of 17%. A second example is a blend of linear styrene-isoprene-styrene triblock copolymer and linear styrene-isoprene diblock copolymer available from Shell Chemical as KRATON® D-1117 and which has a bound styrene content of about 17% and a diblock content of 33%.

An example of a suitable hydrogenated styrene-diene copolymer is a thermoplastic elastomer comprising a blend of clear linear triblock and diblock copolymer based on styrene and ethylene-butylene with a bound styrene of 14% mass. Such a material is commercially available from Shell Chemical Company as KRATON® G-1657. Another example is KRATON® G-1652 from Shell Chemical Company, which is a thermoplastic elastomer comprised of a clear linear triblock copolymer based on styrene and ethylene-butylene, S-E/B-S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer. Such a material is available from Shell Chemical Company as KRATON® Research Product RP6919. This material has a styrene content of 18%, and isoprene content of 36% and an ethylene-butylene content of 46% by weight. Also, a low styrene synthetic copolymer of butadiene and styrene, commonly called SBR rubber, can be used as a solid rubber.

In one embodiment, the adhesive material includes physically cross-linked domains or areas. In another embodiment, the adhesive material is free of physically cross-linked domains or areas. As used herein, "physically cross-linked" means that the crosslinks in the polymer of which it is comprised is not of a chemical (covalent or ionic) nature but of a physical nature which means that there are areas or domains within the elastomer which have a high crystallinity, i.e., a high glass transition temperature. Physically crosslinked may also be referred to as "pseudo crosslinked". For example, in a styrene-isoprene block copolymer, the polystyrene regions tend to associate into glassy islands or domains. As known in the art, a polymer may include either or both of physical and chemical (covalent or ionic) crosslinks. Thus, in some embodiments of the present invention, the polymers of the adhesive material may comprise either or both of physical or chemical crosslinks. In one embodiment, only physical crosslinks are present. In another embodiment, only chemical crosslinks are present.

In one embodiment, the adhesive material includes a silicone-based pressure-sensitive adhesive. Useful silicone pressure sensitive adhesives include those commercially available from Dow Corning Corp., Medical Products and those available from General Electric. Examples of silicone adhesives available from Dow Corning include those sold under the trade names BIO-PSA X7-3027, BIO-PSA X7-4919, BIO-PSA X7-2685, BIO-PSA X7-3122 and BIO-PSA X7-4502. Additional examples of silicone pressure sensitive adhesives useful in the present invention are described in U.S. Pat. Nos. 4,591,622, 4,584,355, 4,585,836 and 4,655,767.

In one embodiment, liquid rubbers may be added to the adhesive material to adjust or control the adhesive or other characteristics. Liquid rubbers useful in this embodiment of the invention include synthetic liquid isoprene rubber, depolymerized natural rubber, various functionally terminated synthetic liquid isoprene-styrene rubbers and liquid isoprene rubbers, liquid isoprene-styrene copolymer, liquid isoprene-butadiene copolymer, liquid butadiene-styrene copolymer and hydrogenated versions of these materials such as liquid ethylene-propylene-styrene. These liquid rubbers are generally compatible with the solid rubber. The liquid rubbers typically have a molecular weight of 25,000 to 50,000, a glass transition temperature of less than −50° C., and a viscosity at 38° C. of 50 to 10,000 Pas. A block copolymer of styrene and isoprene having a styrene content of about 13% and an isoprene content of about 87%, a glass transition of about −60° C., a melt viscosity of about 240 Pas at 50° C. and which is commercially available from Shell Chemical Company as LVSI101, is particularly useful in the practice of the invention. Within the adhesive material, in one embodiment, the weight ratio of solid rubber to liquid rubber is in the range from about 100:1 to about 1:2, and is varied in order to obtain the desired degree of adhesiveness and tackiness. In one embodiment, the weight ratio of solid rubber to liquid rubber is in the range from about 50:1 to about 5:1, and in another embodiment, from about 20:1 to about 10:1.

In one embodiment, the adhesive material may also include a tackifier, as disclosed above.

In one embodiment, the adhesive material is free of any added tackifier.

In other embodiments, additional materials may be included in the adhesive material to modify the properties as needed for certain uses. The quantities to be added depend on the particular uses for which the dressings are to be put. Materials such as low molecular weight polyolefins, for example, polybutenes, commercially available under the tradename PARAPOL® 1300 (Exxon) or low molecular weight polyisobutylenes, commercially available under the tradenames HYVIS® 30 or INDOPOL® (BP), rubbers such as butyl rubber and high molecular weight polyisobutylene, mineral oil, and small amounts of other optional ingredients may be added. The optional low molecular weight polyisobutylene may, for example, be selected from one or more low molecular weight polyisobutylenes having a viscosity average molecular weight of from 36,000 to 70,000. Such polyisobutylenes are commercially available under the trademark VISTANEX® from Exxon Chemical as grades LMMS, LMMH and LMH, having viscosity average molecular weights of about 45,000, 53,000 and 63,000 respectively. The optional low molecular weight polyisobutylene may be present in an amount corresponding to from 0 wt % to about 80 wt % of the adhesive material.

Optionally, an elastomeric polymer such as butyl rubber or high molecular weight polyisobutylene may also be blended into the adhesive material. The optional butyl rubber may be used in the viscosity average molecular weight range of 200,000 to 600,000 and is exemplified by the grades Butyl 065 or Butyl 077, both available from Exxon Chemical. The optional high molecular weight polyisobutylene may be used in the viscosity average molecular weight range of 800,000 to 2,500,000 and is exemplified by the VISTANEX® MM series of products, available from Exxon Chemical, with the MM L-80 grade being a preferred grade for the optional high molecular weight polyisobutylene. The optional high molecular weight rubbers, blended as is indicated above, may be added in amounts suitable to modify various properties of the final formulation and may be from 0% to about 50% of the total weight of the adhesive material, and in one embodiment from about 0.5% to about 25% of the total weight of the adhesive material, and in one embodiment from about 5% to about 10% of the total weight of the adhesive material. The optional low molecular weight polybutenes and/or mineral oil may be added in amounts from 0% to about 20% of the weight of the adhesive material and in one embodiment from about 0.5% to about 10% of the total weight of the adhesive material, and in one embodiment from about 0.5% to about 5% of the total weight of the adhesive material.

Another optional ingredient is a polymer stabilizer. The addition of polymer stabilizers can be advantageous, to protect an unsaturated elastomer from degradation during processing. Suitable stabilizers useful in the practice of the invention include those normally indicated for use with styrenic elastomers such as organophosphites and the so-called hindered phenols, but any suitable stabilizers may be employed. An example of an organophosphite stabilizer is tris(nonylphenyl) phosphite, available as POLYGARD® HR, manufactured by Uniroyal. Particularly useful are the hindered phenols, IRGANOX® 1010 and IRGANOX® 565, manufactured by Ciba-Geigy Corporation. IRGANOX® 1010 is benzenepropanoic acid, 3,5-bis(1,1-dimethylethyl)-4-hydroxy-2,2-bis[[3-[3,5-bis(1,1-dimethylethyl)-4-hydroxyphenol]-1-oxopropoxy]methyl]-1,3-propanediyl ester. IRGANOX® 565 is 4-[[4,6-bis(octylthio)-1,3,5-triazine-2-yl]amino]-2,6-bis (1,1-dimethylethyl)-phenol. Stabilizers may be used separately or in combination, and suitable ranges are within about 0.1% to about 1.5%, and in one embodiment, from about 0.3% to about 1%, by weight based on the total formulation. When present, the stabilizers are generally added to the adhesive material, as is shown in the examples.

Water-Soluble and/or Water-Swellable Polymer

In one embodiment, the water-soluble and/or water-swellable polymer comprises one or more hydrophilic absorbent polymers that are soluble or which absorb and/or are swellable in water. In one embodiment, the hydrophilic absorbent polymers include one or more of alginic acid, sodium alginate, calcium alginate, cellulose-derived material, starch or a modified starch, a copolymer of a starch or a cellulosic material, a water soluble hydrocolloid, a synthetic resin, a mannan, seaweeds, and a plant mucilage. One or more such hydrophilic absorbent polymers may be present and a mixture of soluble and insoluble hydrophilic absorbent polymers can be used. Suitable swellable hydrophilic absorbent polymers include, e.g., cross-linked sodium carboxymethyl cellulose, crystalline sodium carboxymethyl cellulose, cross-linked dextran and starch-acrylonitrile graft copolymer. Others are discussed below. The swellable polymer may also be a so-called "super absorbent" material such as starch sodium polyacrylate. In one embodiment, the swellable polymer is other than a "super absorbent" material. Other hydrophilic absorbent polymers such as gluten and polymers of methyl vinyl ether and maleic acid and derivatives thereof may also be included with the water-soluble and/or water-swellable polymer.

In one embodiment, the water-soluble and/or water-swellable polymer comprises one or more hydrophilic absorbent polymers. In one embodiment, the hydrophilic absorbent polymer includes one or more of alginic acid, sodium or calcium alginate, a carboxymethyl cellulose salt (e.g., sodium, calcium, or other alkali or alkaline earth ions), a water soluble hydrocolloid, a cross-linked carboxymethyl cellulose salt, a crystalline carboxymethyl cellulose salt, a cross-linked dextrin, a starch-acrylonitrile graft copolymer, a starch polyacrylate salt, a water soluble gum, for example, pectin, guar gum or xanthene gum, gelatin, polysaccharides and the like.

In one embodiment, the water-soluble and/or water-swellable polymer may comprise one or more water-soluble hydrocolloids, alone or blended with one or more swellable polymers. Such soluble hydrocolloids include naturally derived products such as pectin, gelatin, starches, guar gum, locust bean gum, gum arabic, gum karaya, collagen, karaya gum, alginic acid and its sodium and/or calcium salts. Also useful are the synthetic hydrocolloids such as sodium carboxymethyl cellulose, crosslinked sodium carboxymethyl cellulose, polyvinyl alcohol, polyvinyl pyrrolidone, high molecular weight polyethylene glycols and polypropylene glycols.

In one embodiment, the water-soluble and/or water-swellable polymer may comprise one or more of, e.g., starches such as flour starch, corn starch, potato starch, etc. In another embodiment, mannan such as yeast gum, manna or konjak may be included. In another embodiment, the water-soluble and/or water-swellable polymer may comprise one or more of various seaweeds such as agar-agar, sodium alginate, etc. In another embodiment, the water-soluble and/or water-swellable polymer may comprise one or more plant mucilages such as tragacanth gum, gum arabic, karaya gum, guar gum, psyllium seed gum, dammar gum, pectin etc., various proteins such as gelatin, collagen, casein, etc. In another embodiment, the water-soluble and/or water-swellable polymer may comprise one or more cellulose-derived materials such as carboxymethyl cellulose, hydroxy-ethyl cellulose, methyl cellulose, etc., modified starches such as soluble starch, carboxymethyl starch, dialdehyde starch, a cross-linked dextrin, etc. In another embodiment, the water-soluble and/or water-swellable polymer may comprise one or more copolymers of starch or cellulose, such as starch-acrylonitrile graft copolymer, a starch polyacrylate salt. In another embodiment, the water-soluble and/or water-swellable polymer may comprise one or more synthetic resins such as polyvinyl alcohol, sodium polyacrylate, polyethylene oxide, etc., and copolymers of starches or celluloses and acrylonitrile, acrylic acid, methacrylic acid, vinyl alcohol, vinyl chloride, etc. In some embodiment, the water-soluble and/or water-swellable polymer may comprise one or more of plant mucilages such as tragacanth gum, gum arabic, karaya gum, guar gum, psyllium seed gum, dammar gum, pectin, etc., the celluloses such as CMC (carboxymethyl cellulose), HEC (hydroxyethl cellulose), etc., and the copolymers of starches or celluloses and acrylonitrile, acrylic acid, sulfuric acid, vinyl sulfonate, etc. The foregoing embodiments may be combined with one another, and may be combined with water swellable polymers and/or super-absorbent materials.

In one embodiment, the water swellable polymers include, for example, hydroxypropylcellulose (HPC) and polyethylene oxide (PEO). HPC is available from commercial suppliers including, for example, Aqualon, Inc., (Wilmington, Del.). The useful HPC generally has an average molecular weight in the range of about 60,000 to 1,200,000. In another embodiment, the water swellable polymer includes homopolymers and copolymers of carboxymethyl cellulose, hydroxyethyl cellulose, hydroxymethyl cellulose). In another embodiment, the water swellable polymer includes a water-soluble or water-swellable polymer derived from acrylic acid or a pharmaceutically acceptable salt thereof, such as the polyacrylic acid polymers as follows: Polycarbophil (Noveon AA-1), carbomer (Carbopol 974P or 971P or 907), or a water-soluble salt of a co-polymer of methyl vinyl ether and maleic acid or anhydride (Gantrez MS-955).

The amount of hydrophilic absorbent polymer, the water-soluble and/or water-swellable polymer, may be from about 10% to about 70% of the total weight of the fluid-absorbing hydrogel pressure-sensitive adhesive material, in one embodiment from about 20% to about 55% of the total weight of the fluid-absorbing pressure-sensitive adhesive material.

The hydrophilic polymer functions as the absorbent, and to help provide the "wet tack" that ensures the adhesive adheres to the skin and to mucous membranes when they are moist.

In one embodiment, the hydrophilic polymer is capable of swelling in water and transporting water.

Release Liner

In one embodiment, the pressure-sensitive adhesive includes a release-coated liner on the skin-contacting side, which is retained in place prior to use and is removed just prior to application to the patient's skin. The release-coated liner may be any release-coated liner known in the art which is compatible with the particular pressure-sensitive adhesive selected for use the dressing.

The release-coated liner may comprise a substrate sheet of paper, polymer film or combinations thereof coated with a release composition. The typical release coating used in the industry is a silicone-based molecule which can be cured either thermally or with irradiation energy such as ultraviolet light or electron beam. Paper substrates are useful because of the wide variety of applications in which they can be employed. Paper is also relatively inexpensive and has desirable properties such as antiblocking, antistatic, dimensional stability, and can potentially be recycled. Any type of paper having sufficient tensile strength to be handled in conventional paper coating and treating apparatus can be employed as the substrate layer. Thus, any type of paper can be used depending upon the end use and particular personal preferences. Included among the types of paper which can be used is paper, clay coated paper, glassine, polymer coated paper, paperboard from straw, bark, wood, cotton, flax, cornstalks, sugarcane, bagasse, bamboo, hemp, and similar cellulose materials prepared by such processes as the soda, sulfite or sulfate processes, the neutral sulfide cooking process, alkali-chlorine processes, nitric acid processes, semi-chemical processes, etc. Although paper of any weight can be employed as a substrate material, paper having weights in the range of from about 30 to about 120 pounds per ream are useful, and papers having weights in the range of from about 60 to about 100 pounds per ream are presently preferred. The term "ream" as used herein equals 3000 square feet. Examples of specific papers which can be utilized as substrates in preparing the deposit laminates of the present invention include 41-pound offset grade bleached Kraft; 78-pound bleached Kraft paper, etc.

Alternatively, the substrate of the release-coated liner may be a polymer film, and examples of polymer films include polyolefin, polyester, polyvinyl chloride, polyvinyl fluoride (PVF), polyvinylidene difluoride (PVDF), etc., and combinations thereof. The polyolefin films may comprise polymer and copolymers of monoolefins having from 2 to 12 carbon atoms or from 2 to about 4 or 8 carbon atoms per molecule. Examples of such homopolymers include polyethylene, polypropylene, poly-1-butene, etc. The examples of copolymers within the above definition include copolymers of ethylene with from about 1% to about 10% by weight of propylene, copolymers of propylene with about 1% to about 10% by weight of ethylene or 1-butene, etc. Films prepared from blends of copolymers or blends of copolymers with homopolymers also are useful. In addition films may be extruded in mono or multilayers.

A third type of material used as a substrate for the release liner is a polycoated kraft liner which is basically comprised of a kraft liner that is coated on either one or both sides with a polymer coating. The polymer coating, which can be comprised of high, medium, or low density polyethylene, propylene, polyester, and other similar polymer films, is coated onto the substrate surface to add strength and/or dimensional stability to the liner. The weight of these types of liners ranges from 30 to 100 pounds per ream, with 40 to 94 pounds per ream representing a typical range. In total, the final liner is comprised of between 10% and 40% polymer and from 60% to 90% paper. For two sided coatings, the quantity of polymer is approximately evenly divided between the top and bottom surface of the paper.

The release coating which is contained on the substrate to form the release-coated liner may be any release coating known in the art. Silicone release coatings are particularly useful, and any of the silicone release coating compositions which are known in the art can be used. In one embodiment, it is desired to have a release coating having a smooth surface.

Conductive Fibers

As used herein, the term "conductive fiber" refers to any electrically conductive fiber which also generates palpable heat when current passes through the fiber, i.e., a fiber which exhibits resistive heating. In one embodiment, the conductive fiber may include any electrically conductive fiber capable of generating heat when a relatively low voltage is applied. Such fibers are conductive, but have sufficient resistance that heat is generated by the passage of the current from a relatively low voltage source, such as a voltage less than about 100 volts, and in one embodiment less than about 50 volts, and in another embodiment, less than about 25 volts, and in another embodiment, less than about 16 volts, and in another embodiment about 9 volts or less.

In one embodiment, the conductive fiber may include metal fibers, carbon fibers, graphite fibers or carbon/graphite fibers. In another embodiment, the conductive fiber may comprise non-conductive fiber material which is impregnated or filled with electrically conductive particles, fibers or layers of an electrically conductive material.

In one embodiment, the metal fibers may comprise any conductive metal fiber which generates heat when a current is passed through it. The metal fiber may have a diameter as low as 1 μm. In another embodiment, the conductive fiber may be metal coated thread, that is a thread or fiber coated with at least one of the highly conductive metals, such as silver, gold, copper, tin, nickel, zinc, palladium, alloys and combinations thereof. Such coating may be applied on a carbon/graphite thread, an extruded polymer filament, synthetic threads or fibers, fiberglass or ceramic threads or fibers. The metal may be applied to such threads, filaments and fibers by sputtering, electroplating, electroless deposition, or by any other appropriate metal coating or impregnating technique.

In one embodiment, any of the above-mentioned threads, filaments and fibers may be impregnated with carbon or graphite. Thus, the conductive fibers may contain carbon or graphite inside the polymer fiber or synthetic polymer or may be ceramic fibers or thread coated or impregnated with carbon or carbon/graphite-containing material to make the threads or fibers conductive.

In one embodiment, the conductive particles may include other conductive materials, such as indium tin oxide (ITO), and materials such as metal nitrides (e.g., TiN, WN, etc.), metals such as Mo, W, Al, and alloys (e.g., TiW) and various other materials used in the semiconductor industry as conductors, such as silicides $MoSi_2$, $TiSi_2$, $TaSi_2$, $WSi_2$, or $CoSi_2$.

In one embodiment, the conductive fibers are encapsulated by insulating materials, forming continuous heating cables. In another embodiment, the conductive fibers include individually insulated electrically conductive carbon or metal containing threads/fibers or metal wires that are woven together with nonconductive threads, into sheets, sleeves or strips. The individually insulated conductive threads/fibers or metal wires can be laminated between layers of the pressure-sensitive adhesive.

Carbon Fibers

Any suitable conductive, heat-generating carbon fibers can be used.

In one embodiment, the carbon fibers are made from a polyacrylonitrile precursor. In another embodiment, the carbon fibers may be pitch-based. Polyacrylonitrile-based carbon fibers are commercially available as FORTAFIL® carbon fiber, available from Fortafil Fibers, Inc., Knoxyille, Tenn. and as SIGRAFIL® C, available from SGL Carbon AG, Wiesbaden, Germany. Thornel® carbon fibers are available from CYTEC Industries, Inc., West Paterson, N.J., in both polyacrylonitrile-source and pitch-source types.

In one embodiment, the carbon fibers may be provided in the form of a web, which can be prepared by appropriate thermal treatment of a polyacrylonitrile fabric.

In one embodiment, the conductive fibers range from about 0.001 mm (1 micron) to about 0.5 mm (500 microns) in diameter. In another embodiment, the conductive fibers range from about 0.005 mm (5 microns) to about 0.1 mm (100 microns). In another embodiment, the conductive fibers range from about 0.01 mm (10 microns) to about 0.05 mm (50 microns). With reference to the conductive fibers, the term "diameter" is used to refer to the largest cross-sectional dimension of the conductive fibers, which may or may not be generally round in cross-sectional shape. The cross-sectional shape of the conductive fibers is not limited, and may include round, elliptical, polygonal or other or variable cross-sectional shapes.

Source of Electrical Energy

The source of electrical energy can be any suitable source of low voltage electrical energy, such as a battery, a fuel-cell, a transformed/rectified AC line current in which the AC line voltage is reduced by a transformer and optionally rectified to DC.

In one embodiment, the source of electrical energy is a thin film primary battery. Many thin film batteries are known in the art, and any thin film battery may be suitable for use with the present invention. In one embodiment, the thin film battery is at least partially flexible, and in one embodiment, is substantially flexible, thus not inhibiting the desired flexibility of the heatable dressing in one embodiment of the present invention.

In one embodiment, the thin film battery is one such as disclosed in U.S. Pat. No. 6,045,942, the disclosure of which is incorporated herein by reference in its entirety. Thus, in one embodiment, the source of electrical energy is a thin film primary battery including a non-conductive film substrate, thin film electrodes printed upon the substrate, aqueous electrolyte, and a sealing thin film layer sealing the battery, in which the thin film electrodes are prepared including the steps of printing electrically conductive ink onto the substrate, embedding active electrode material into the wet surface of the printed conductive ink and drying the conductive ink, as described in the '942 patent. In one such embodiment, a common cathodic electrode is employed with two or more chemically different anodic electrodes to allow for multiple voltage outputs from the same battery, and in another embodiment, a common anodic electrode is employed with two or more chemically different cathodic electrodes to allow for multiple voltage outputs from the same battery.

In another embodiment, the source of electrical energy is a thin film battery including a pair of confronting non-conductive film substrates, a cathodic thin film electrode printed upon one of the substrates and an anodic thin film electrode printed on the other substrate, the orientation of the anodic and cathodic electrodes on the respective substrates being staggered so that they lie substantially in the same plane and are separated by a gap substantially filled with an aqueous electrolyte disposed between the substrates, as described in U.S. Pat. No. 6,045,942. In one such embodiment, a common cathodic electrode is employed with two or more chemically different anodic electrodes to allow for multiple voltage outputs from the same battery, and in another embodiment, a common anodic electrode is employed with two or more chemically different cathodic electrodes to allow for multiple voltage outputs from the same battery.

In other embodiments, other known thin film batteries may be used as the source of electrical energy.

In one embodiment, the source of electrical energy is a standard dry cell battery. In one embodiment, the source of electrical energy is a Ni—Cd or Nicad battery. In one embodiment, the source of electrical energy is a nickel-metal hydride or NiMH battery. In one embodiment, the source of electrical energy is a mercury battery. As noted, the foregoing battery types are merely exemplary, and the present invention need not be limited to any particular battery.

It is noted that in one embodiment, a thin film battery may be applied to the dressing as an additional layer or, in another embodiment, a thin film battery may be applied and function as the backing layer 106 in the dressing 100. In such embodiments, the dressing 100 is unencumbered by a separate battery.

Electrical Connections

The electrical connections to the conductive fibers may be made in any suitable manner. As shown in FIGS. 1-4, the electrical conductor 108 is in contact with at least a portion of the conductive fibers 104. As noted above, in some embodiments, the electrical conductor 108 is not in direct contact with all of the conductive fibers. In one such embodiment, the electrical conductor The electrical conductor may be of copper or other electrically conductive metal foil, strip or woven wire braid or a molded conductive plastic conductor. Consistent with the need to provide electrical contact to the conductive fibers, the electrical conductor may have a protective coating to reduce oxidation and other forms of corrosion of the electrical conductor.

The electrical conductor may be attached directly to the conductive fibers. In one embodiment, conductive plastics or silicone elastomers may be used as cements for the electrical conductors, as needed.

In another embodiment, the electrical conductors can be attached to the conductive fibers by an electrically conductive self adhesive tape or on an electrically conductive silicone elastomer or caulk. In one embodiment, the pressure-sensitive adhesive maintains contact between the electrical conductor and the conductive fibers.

As described above, in some embodiments, the electrical connections include a switch, such as the switch 122 shown in FIG. 4. In one embodiment, the electrical connection is made to the dressing 100 from the source of electrical energy 112 with no separate thermostatic temperature control device included as part of the dressing 100.

Backing Layer

In one embodiment, the heatable dressing 100 includes a backing layer 106 on the side 118 opposite the skin-contacting side 116 of the dressing 100. As noted above, in one embodiment, the backing layer 106 is formed by a thin film battery, which thereby serves the dual purpose of serving as the source of electrical energy and forming the backing layer 106. In another embodiment, the backing layer 106 includes a layer formed by a thin film battery, which thereby may combine with another layer, such as one of those described below, and serves the dual purpose of serving as the source of electrical energy and forming a portion of the backing layer 106.

Figure 6:
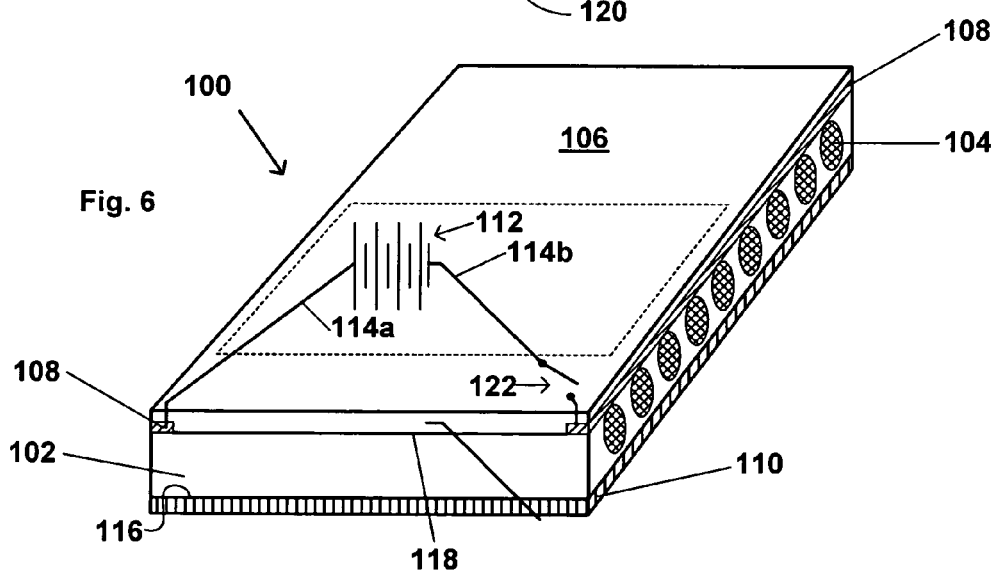
FIG. 6 is a schematic perspective view of an embodiment of a skin-contacting heatable dressing similar to the embodiment shown in FIG. 5, but including a source of electrical energy in the backing layer.

FIG. 6 is a schematic perspective view of an embodiment of a skin-contacting heatable dressing similar to the embodiment shown in FIG. 5, but including a source of electrical energy 112 in the backing layer 106. As shown in FIG. 6, the source of electrical energy 112 is embedded within the backing layer, as shown schematically by the dashed lines. As in other embodiments, the source of electrical energy 112 is connected to the conductive electrical leads 108 by electrical lead wires 114a, 114b and, in one embodiment, includes a switch 122. In this embodiment, the source of electrical energy 112 is an integral part of the backing layer 106 or may be considered to replace the backing layer 106.

Figures 7, 8:
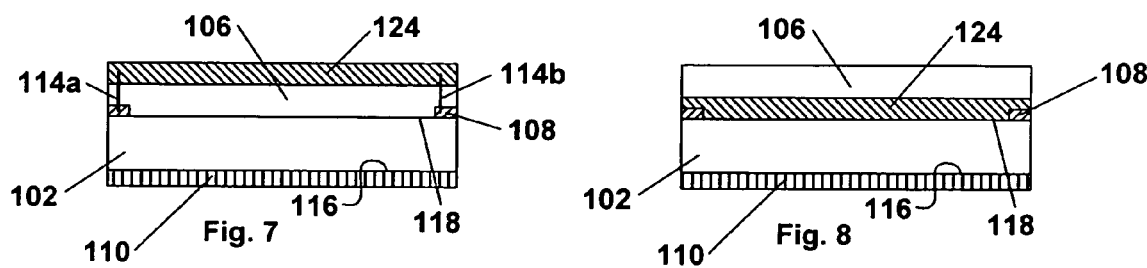
FIGS. 7 and 8 are schematic cross-sectional views of two further embodiments including a thin film battery or other source of electrical energy in accordance with the present invention.

As noted, in another embodiment, the source of electrical energy 112 may be provided in a layer separate from and in addition to the backing layer 106. FIGS. 7 and 8 are schematic cross-sectional views of two further embodiments including a thin film battery or other source of electrical energy as a separate layer 124 in addition to the backing layer 106, in accordance with the present invention.

In one embodiment, shown schematically in FIG. 7, a separate layer 124 formed by the source of electrical energy 112 is positioned above the backing layer 106, i.e., the backing layer 106 is between the adhesive layer 102 and the source of electrical energy 112. In this embodiment, the electrical lead wires 114a, 114b are used to make electrical connection from the layer 124 to the conductive electrical leads 108.

In another embodiment, shown schematically in FIG. 8, a separate layer 124 formed by the source of electrical energy 112 is positioned between the backing layer 106 and the adhesive layer 102, i.e., in contact with the adhesive layer 102. In this embodiment, the source of electrical energy 112 may be electrically attached directly to the conductive electrical leads 108, without use of the electrical lead wires 114a, 114b.

In one embodiment, the backing layer is an insulating material, such as a foam or a fabric. In one embodiment, the backing layer is a heat-reflecting material such as a metal foil, for example and aluminum foil or an aluminized polymer, such as PET, for example, an aluminized MYLAR®. In one embodiment, the backing layer is a liquid-impermeable film.

In one embodiment, the backing layer comprises one or more layers of one or more of polyurethane, polyethylene, polybutadiene, polyvinylchloride, polyvinylidenechloride, polyvinylalcohol, polyacrylate, polysulphone, polystyrene, polypropylene, polyamide, ethylene-vinylacetate-copolymer, polyester, polycarbonate, polyvinylfluoride, copolyesterether, synthetic rubbers, silicone, and mixtures thereof. When the backing layer comprises one of these polymeric materials, in one embodiment, the backing layer further comprises various known additives, such as an anti-blocking agent, e.g., $SiO_2$, talc or other known anti-blocking agents, plasticizers, fillers and pigments.

Medicaments

In one embodiment, the pressure-sensitive adhesive contains one or more medicament capable of being transdermally absorbed or delivered onto the skin surface. In one embodiment, application of heat from the conductive fibers enhances transdermal absorption of at least one of the one or more medicament. As used herein, the term "medicament" refers to a composition comprising at least one active ingredient, which may be added to the pressure-sensitive adhesive layer together with a pharmaceutically acceptable vehicle suitable for cutaneous application. In certain embodiments, the medicament may further comprise one or more excipients including, but not limited to preservatives, antioxidants, moisturizers, emollients, buffering agents, solubilizing agents, penetration enhancers, skin protectants, and mixtures thereof.

In one embodiment, the medicament which may be included in the pressure-sensitive adhesive layer 102 is one or more of a local anesthetic, a non-steroidal anti-inflammatory drug, an opioid, an N-methyl-D-aspartate antagonist, a steroid, a corticosteroid, a tricyclic antidepressant, and mixtures thereof. In one embodiment, the medicament may be any pharmaceutically active ingredient or drug which is capable of transdermal absorption. A number of possible medicaments are listed in U.S. Patent Application Publication No. 2003/0139698, the disclosure of which relating to transdermally absorbable medicaments is incorporated herein by reference.

As known in the art, not all medicaments are capable of transdermal administration. The mammalian skin presents a significant barrier to the environment, so only some medicaments are included in this group. Those of skill in the pharmaceutical art can suitably determine and select which medicaments are capable of such administration.

The present inventor has discovered that by application of heat from the presently disclosed skin-contacting heatable dressing, the absorption of transdermally absorbable medicaments generally can be enhanced. Either or both of the rate and the quantity of medicament absorbed can be increased by application of heat, compared to absorption of the same medicament from the same vehicle without the application of heat. In one embodiment of the present invention, the vehicle carrying the medicament and from which the medicament is absorbed is the pressure-sensitive adhesive layer 102. However, it is possible to include additional materials in the pressure-sensitive adhesive layer 102 to enhance absorption of the medicament from the pressure-sensitive adhesive layer 102, or to assist in dispersion of the medicament in the pressure-sensitive adhesive layer 102. The nature of any such additives to the pressure-sensitive adhesive vehicle selected is defined by, for example, the solubility of the active ingredient and/or active ingredients in the pressure-sensitive adhesive vehicle, rate of release of the active ingredient or active ingredients from the pressure-sensitive adhesive vehicle, the facility with which the pressure-sensitive adhesive vehicle hydrates the stratum corneum layer of the skin and thereby improves permeability of the skin barrier to the active ingredient and/or active ingredients, and the stability of the active ingredient and/or active ingredients in the pressure-sensitive adhesive vehicle. The use of selected additives may assist in improving these characteristics. The choice of pressure-sensitive adhesive vehicle for dissolution or suspension of the active ingredient or ingredients is well known in the art (See, for example, Dirk B. Robinson and Howard I. Miabach, Dermatologic Pharmacology in BASIC AND CLINICAL PHARMACOLOGY, 871-87 (Bertram G. Katzung, Ed., Fifth Edition, 1992), which is hereby incorporated by reference in its entirety). In one embodiment, the presence of one or more additives such as penetration enhancers, described below, in the pressure-sensitive adhesive vehicle also affects the rate of diffusion of the one or more active ingredient of the medicament into and across the skin barrier.

In certain embodiments of the present invention, the medicament may include one or more excipient such as a preservative, an antioxidant, a moisturizer, an emollient, a buffering agent, a solubilizing agent, a penetration enhancer, and a skin protectant (see, for example, (Monica Ramchandani and Rohinton Toddywala, Formulation of Topical Drug Delivery Systems, in TRANSDERMAL AND TOPICAL DRUG DELIVERY SYSTEMS, 539-92 (Tapash K. Ghosh, William R. Pfister and Sull Yum, Eds. 1997, which is hereby incorporated by reference in its entirety).

In certain embodiments, the medicament may include one or more skin penetration enhancer to facilitate or enable intradermal and transdermal delivery of one or more active ingredients of the medicament. Penetration enhancers may chemically modify the skin in a manner that decreases the barrier properties of the skin. Penetration enhancers should act rapidly and reversibly, should be non-toxic, non-allergenic, non-irritating, and pharmacologically inert (Tapash K. Ghosh and William R. Pfister Transdermal and Topical Delivery Systems: An Overview and Future Trends, in TRANSDERMAL AND TOPICAL DRUG DELIVERY SYSTEMS, 1-32 (Tapash K. Ghosh, William R. Pfister and Sull Yum, Eds. 1997, which is hereby incorporated by reference in its entirety). Suitable penetration enhancers and typical concentrations (expressed as w/w %) include, but are not limited to: propylene glycol (5%-80%), alcohols (including ethanol and lauryl alcohol) (0.5%-30%), esters such as glycerol monolaurate (1%-10%), salicylic acid (1%-5%), anionic surfactants such as sodium dodecyl sulfate (1%-10%), cationic surfactants such as cetyltrimethyl ammonium bromide (1%-10%), nonionic surfactants such as polysorbates (1%-10%), phospholipids (1%-10%), urea (1%-5%), and mixtures thereof.

Method of Making the Heatable Dressing

In one embodiment, the present invention relates to a method of making a skin-contacting heatable dressing including providing a substrate; applying a plurality of heat generating conductive fibers to the substrate; applying a pressure-sensitive adhesive layer over the plurality of heat generating conductive fibers and the substrate, wherein the heat generating conductive fibers are substantially embedded within the pressure sensitive adhesive layer; and electrically connecting a source of electrical energy to the conductive fibers.

In one embodiment, the substrate is one of a release liner or a backing layer. Where the substrate is a release liner, the side of the pressure-sensitive adhesive contacting the substrate may become the skin-contacting side of the heatable dressing. In this embodiment, when the pressure-sensitive adhesive is applied over the conductive fibers, the fibers may be at least substantially embedded in the pressure-sensitive adhesive, although in another embodiment, it may be helpful to apply some force to the pressure-sensitive adhesive and/or to the substrate, so as to better embed the conductive fibers. In one such embodiment, when the pressure-sensitive adhesive has been applied, a backing layer may be applied either before or after the source of electrical energy is provided. In one embodiment, as described above, the source of electrical energy is a thin film battery. In one embodiment, the thin film battery is applied as a layer in addition to the backing layer, and in another embodiment, the thin film battery is applied and acts as the backing layer.

In an embodiment in which the substrate is the backing layer, the pressure-sensitive adhesive may be applied prior to application of the conductive fibers. In this embodiment, the pressure-sensitive adhesive layer may be permanently attached to the backing layer. In this embodiment, when the conductive fibers are applied to the pressure-sensitive adhesive layer, another substrate, such as a release liner, may be used to at least substantially embed the fibers into the pressure-sensitive adhesive. As with the embodiment described above, it may be helpful to apply some force to the pressure-sensitive adhesive layer and/or to the substrate and/or another substrate, in order to embed the conductive fibers.

In one embodiment, the method further includes applying conductive electrical leads in contact with the conductive fibers and providing electrical contact between the conductive electrical leads and the source of electrical energy. In one embodiment, two of the conductive electrical leads are applied along each of two opposite lateral edges with the conductive fibers providing electrical connection between the two conductive electrical leads.

In one embodiment, the conductive fibers may be applied to the substrate by a printing process. In one embodiment, the conductive electrical leads may be applied by a printing process. In one embodiment, the electrical lead wires may be applied by a printing process. Suitable printing processes are known in the art for applying conductive materials to various substrates.

In one embodiment, one or more medicaments capable of being transdermally absorbed are added to the pressure-sensitive adhesive. Such medicaments have been described herein. Methods for mixing or combining or applying such medicaments to materials such as pressure-sensitive adhesives are known in the art and may be suitable selected.

Figure 10:
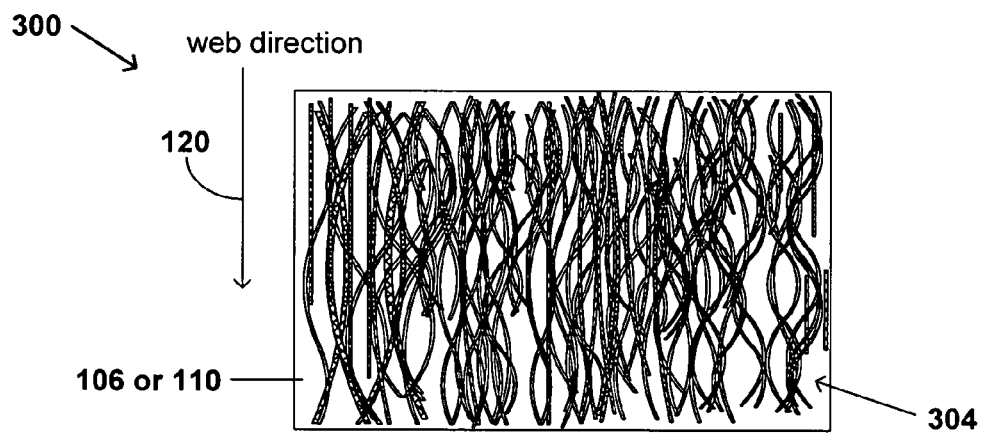
FIGS. 10 and 11 are schematic plan views of portions of the heatable dressing in accordance with an embodiment of the present invention, at two points in a process of making the dressing.
Figure 11:
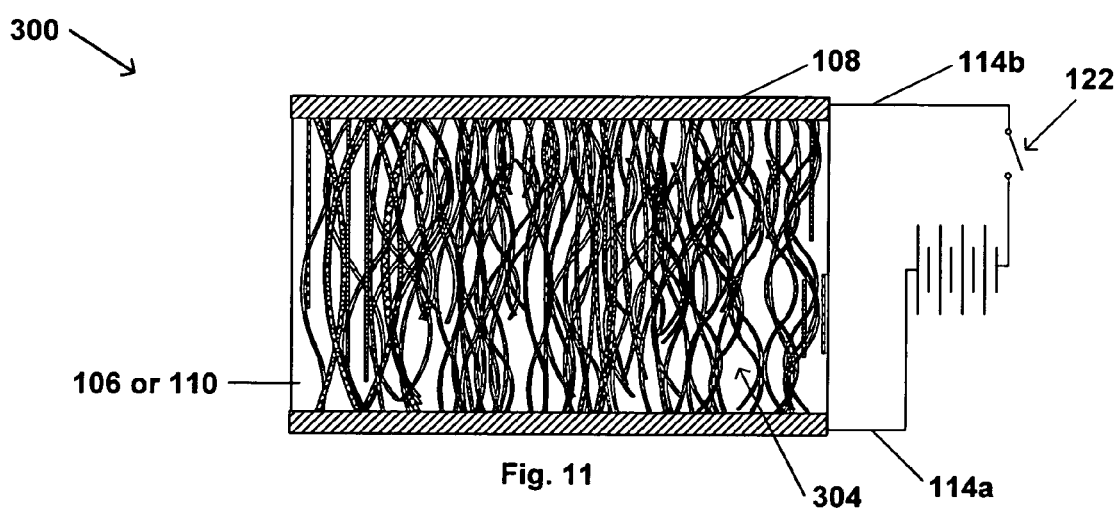

FIGS. 10 and 11 are schematic plan views of portions of a heatable dressing 300 in accordance with an embodiment of the present invention, at two points in a process of making the dressing 300. FIGS. 10 and 11 depict an embodiment of the dressing 300 which includes a plurality of conductive fibers 304, in which the fibers 304 overlap one another, include some fibers shorter than others, some fibers that reach across from one side to the other, and many, but not all, of which are in contact with the conductive electrical leads 108. A plan view of the embodiment depicted in FIG. 9 would be similar to the embodiment depicted in FIGS. 10 and 11.

FIG. 10 depicts a substrate, which in one embodiment may be a backing layer 106, and in another embodiment may be a release liner 110, upon which a plurality of conductive fibers 304 have been deposited. As noted above, the conductive fibers may be deposited by a variety of different methods. The substrate (106 or 110 or other), as shown in FIG. 10, in one embodiment, is a portion of a continuous web, upon which the conductive fibers 304 are continuously applied.

FIG. 11 depicts the substrate 106 or 110 with conductive fibers 304 in place, following steps of applying the conductive electrical leads 108 and attaching a source of electrical energy 112 to the leads 108 by means of the electrical lead wires 114a, 114b. In this embodiment, the pressure-sensitive adhesive layer is next applied, followed by application of another substrate layer, which may be, for example, a backing layer or a release liner layer or a layer formed by a thin film battery.

As noted above, the steps of methods of making the heatable dressing may be carried out in various sequences, and the embodiment depicted in FIGS. 10 and 11 is illustrative of but one such method. For example, the leads 108 may be laid down prior to the conductive fibers 304, or the pressure-sensitive adhesive may be deposited on the substrate first, followed by deposition of the conductive fibers 304 and then the leads 108, or followed by deposition of the leads 108 and then the conductive fibers 304.

In one embodiment, the conductive fibers may be formed by a printing process. Any suitable printing process known in the art may be used for forming the conductive fibers. In one embodiment, the heat generating material and the conductive electrical leads are printed on a backing layer, followed by application of the pressure-sensitive adhesive and a release liner, followed by suitable lamination or by application of additional pressure-sensitive adhesive material and a release liner, followed by suitable lamination. In another embodiment, the heat generating material and the conductive electrical leads are printed on a pressure-sensitive adhesive layer which has been formed on a release liner, followed by application of the backing layer and suitable lamination.

In one embodiment, the conductive fibers may be produced by printing conductive traces on the support with a conductive polymeric composition. Typically, the polymeric material comprises a conductive filler which is dispersed in a resin formulation that includes solvents to reduce viscosity. The resulting conductive polymeric material is extruded in its uncured state through a suitable apparatus, such as a syringe-like apparatus, which is translated over the substrate, or pressed through a screen printing apparatus, to deposit conductive traces in the desired circuit pattern or screen printed through a pattern created by a stencil. For certain known conductive polymeric materials, traces formed of such materials are periodically cured by heating the material to evaporate the solvents. The conductive filler may be, for example, an electrically conductive particulate material, such as silver, gold, palladium, and nickel. In one embodiment, the conductive particles may include other conductive materials, such as indium tin oxide (ITO), and materials such as metal nitrides and materials used in the semiconductor industry as conductors. The conductive particles may have suitable sizes, for example sizes in the range of about 0.1 micron to about 20 microns. The conductive particles may have any suitable shape, such as spherical, ovoid, elongated, flattened, flaked, needle-shape, etc.

The resin portion of the conductive ink may comprise any suitable polymeric or copolymeric resin, including, for example, a (meth)acrylate, a poly(meth)acrylic acid, linear polyester, vinyl copolymer-based resins, polyhydroxyethers, polyurethanes, etc. The resin portion may be a thermosetting polymer, such as an epoxy or phenolic resin. The conductive ink may be curable by heat or radiation, or may cure simply by evaporation of a suitable solvent. In one embodiment, the solvent is water, and in another, an organic solvent.

In one embodiment, the conductive fibers may be formed by intaglio printing or other similar contact printing process.

In one embodiment, the conductive fibers may be formed by an electroless plating technique.

In one embodiment, the conductive fibers may be formed by sputtering conductive materials onto a substrate, by a CVD or other vapor deposition process, followed by etching to define separate fibers.

In one embodiment, the conductive fibers may be formed by metallizing portions of a polymeric or other non-conductive substrate, followed by electrodeposition of additional conductive fiber material, such as a metal.

EXAMPLE

An exemplary dressing in accordance with an embodiment of the present invention is prepared as follows. Four carbon fibers are placed in parallel arrangement 1 cm apart on a 10 cm×5 cm polyurethane backing material. A solvent-based acrylic adhesive is laminated on the polyurethane backing, so that the fibers are embedded within the adhesive. The fibers are Bekintex fibers from Bekaert Corporation.

Each side of the dressing is connected to a source of electrical energy, which is a variable voltage generator so that it is possible to change voltage and correlate it to temperature. A temperature probe is placed on the surface of the pressure sensitive adhesive to evaluate the temperature of the dressing. A temperature of 37.4° C. is reached with 8 volts applied to the dressing and a temperature of 45.5° C. is reached with 12 volts applied to the dressing.

While the invention has been explained in relation to various of its embodiments, it is to be understood that various modifications thereof will be apparent to those skilled in the art upon reading the specification. The features of the various embodiments of the articles described herein may be combined within an article. The various methods of manufacturing the articles of the present invention described herein may also be combined. Therefore, it is to be understood that the invention disclosed herein is intended to cover such modifications as fall within the scope of the appended claims.

What is claimed is:

1. A skin-contacting heatable dressing comprising:
a pressure-sensitive adhesive layer having a first skin-contacting side and a second side and lateral edges;
palpable heat generating conductive fibers substantially embedded within the skin-contacting pressure sensitive adhesive layer;
a source of electrical energy electrically connected to the conductive fibers and
conductive electrical leads in the pressure sensitive layer providing electrical connection between the electrical energy source and the conductive fibers, wherein the electrical leads are disposed along each of two opposite lateral edges of the pressure sensitive adhesive layer with the conductive fibers providing electrical connection between the electrical leads.

2. The dressing of claim 1, wherein the heat generating conductive fibers comprise one or more of carbon fibers, metal fibers, conductive polymer fibers, non-conductive polymer fibers made conductive by embedding with conductive particles or conductive additives.

3. The dressing of claim 1, further comprising a backing layer on the second side of the pressure-sensitive adhesive layer.

4. The dressing of claim 1, wherein the source of electrical energy is connected to the conductive fibers via an on-off switch.

5. The dressing of claim 1, wherein the dressing is free of a thermostatic temperature control device.

6. The dressing of claim 1, wherein the dressing is flexible and moldable to a desired shape.

7. The dressing of claim 1, wherein the dressing comprises a quantity and/or quality of conductive fibers such that when a selected energy source is applied, the dressing reaches a temperature in the range from about 25° C. to about 40° C.

8. The dressing of claim 7, wherein the temperature is maintained in the range from about 35° C. to about 38.5° C.

9. A method of using a skin-contacting heatable dressing, comprising applying the skin-contacting side of the dressing of claim 1 to a patient in need thereof.

10. A skin-contacting heatable dressing comprising:
a pressure-sensitive adhesive layer having a first skin-contacting side and a second side;
palpable heat generating conductive fibers substantially embedded within the skin-contacting pressure sensitive adhesive layer; and
a source of electrical energy electrically connected to the conductive fibers via an on-off switch, wherein the on-off switch is used to control temperature of the dressing.

11. A skin-contacting heatable dressing comprising:
a pressure-sensitive adhesive layer having a first skin-contacting side and a second side;

heat generating conductive fibers substantially embedded within the skin-contacting pressure sensitive adhesive layer; and a source of electrical energy electrically connected to the conductive fibers, wherein the pressure-sensitive adhesive is a hydrogel or a hydrocolloid.

12. A skin-contacting heatable dressing comprising:
a pressure-sensitive adhesive layer having a first skin-contacting side and a second side;
palpable heat generating conductive fibers substantially embedded within the skin-contacting pressure sensitive adhesive layer; and
a source of electrical energy electrically connected to the conductive fibers, wherein the source of electrical energy is a thin film battery.

13. The dressing of claim 12, wherein the thin film battery forms at least a portion of a backing layer on the second side of the dressing.

14. The dressing of claim 12, wherein the source of electrical energy is a thin film battery contained within a backing layer on the second side of the dressing.

15. The dressing of claim 12, wherein the source of electrical energy is a thin film battery in a separate layer between a backing layer on the second side of the dressing and the pressure-sensitive adhesive layer.

16. The dressing of claim 12 wherein the source of electrical energy is a thin film battery in a separate layer over a backing layer on the second side of the dressing.

17. A skin-contacting heatable dressing comprising:
a pressure-sensitive adhesive layer having a first skin-contacting side and a second side and lateral edges;
palpable heat generating conductive fibers substantially embedded within the skin-contacting pressure sensitive adhesive layer;
a backing layer over the second side of the pressure-sensitive adhesive layer;
a source of electrical energy electrically connected to the conductive fibers; and
conductive electrical leads in the pressure sensitive layer providing electrical connection between the electrical energy source and the conductive fibers, wherein the electrical leads are disposed alone each of two opposite lateral edges of the pressure sensitive adhesive layer with the conductive fibers providing electrical connection between the electrical leads.

18. The dressing of claim 17, wherein the heat generating conductive fibers comprise one or more of carbon fibers, metal fibers, conductive polymer fibers, non-conductive polymer fibers made conductive by embedding with conductive particles or conductive additives.

19. A method of using a skin-contacting heatable dressing, comprising applying the skin-contacting side of the dressing of claim 17 to a patient in need thereof.

20. The dressing of claim 17, wherein the pressure-sensitive adhesive is a hydrogel or a hydrocolloid.

21. A skin-contacting heatable dressing comprising:
a pressure-sensitive adhesive layer having a first skin-contacting side and a second side;
palpable heat generating conductive fibers substantially embedded within the skin-contacting pressure sensitive adhesive layer;
a backing layer over the second side of the pressure-sensitive adhesive layer; and
a source of electrical energy electrically connected to the conductive fibers, wherein the source of electrical energy is a thin film battery contained within the backing layer.

22. The dressing of claim 21, wherein the source of electrical energy is a thin film battery in a separate layer between the backing layer and the pressure-sensitive adhesive layer.

23. The dressing of claim 21, wherein the source of electrical energy is a thin film battery in a separate layer over the backing layer.

24. A skin-contacting heatable dressing comprising:
a pressure-sensitive adhesive layer having a first skin-contacting side and a second side, and containing one or more medicament capable of being transdermally absorbed or delivered onto the skin surface;
heat generating conductive fibers substantially embedded within the skin-contacting pressure sensitive adhesive layer; and
a source of electrical energy electrically connected to the conductive fibers.

25. The dressing of claim 24, wherein application of heat from the conductive fibers enhances transdermal absorption of at least one of the one or more medicament.

26. The dressing of claim 24, wherein the medicament is one or more of a local anesthetic, a non-steroidal anti-inflammatory drug, an opioid, an N-methyl-D-aspartate antagonist, a steroid, a corticosteroid, a tricyclic antidepressant, and mixtures thereof.

27. The dressing of claim 24, wherein the heat generating conductive fibers comprise one or more of carbon fibers, metal fibers, conductive polymer fibers, non-conductive polymer fibers made conductive by embedding with conductive particles or conductive additives.

28. The dressing of claim 24, wherein the source of electrical energy is a thin film battery contained within a backing layer on the second side of the dressing.

29. The dressing of claim 24, wherein the source of electrical energy is a thin film battery in a separate layer between a backing layer on the second side of the dressing and the pressure-sensitive adhesive layer.

30. The dressing of claim 24, wherein the source of electrical energy is a thin film battery in a separate layer over a backing layer on the second side of the dressing.

31. A method of using a skin-contacting heatable dressing, comprising applying the skin-contacting side of the dressing of claim 24 to a patient in need thereof.

32. The dressing of claim 24, wherein the pressure-sensitive adhesive is a hydrogel or a hydrocolloid.

33. A method of making a skin-contacting heatable dressing comprising:
providing a substrate;
applying a plurality of palpable heat generating conductive fibers to the substrate;
applying a pressure-sensitive adhesive layer over the plurality of heat generating conductive fibers and the substrate, wherein the heat generating conductive fibers are substantially embedded within the pressure sensitive adhesive layer and extend to opposite lateral edges of the pressure sensitive adhesive layer;
applying at least two conductive electrical leads in contact with the conductive fibers along each of two opposite lateral edges of the pressure sensitive layer, the fibers providing electrical connection between the conductive electrical leads; and
electrically connecting a source of electrical energy to the conductive fibers electrical leads.

34. The method of claim 33, wherein the substrate is one of a release liner or a backing layer.

35. The method of claim 33, wherein the pressure-sensitive adhesive is a hydrogel or a hydrocolloid.

36. A method of making a skin-contacting heatable dressing comprising:
providing a substrate;
applying a plurality of palpable heat generating conductive fibers to the substrate;
applying a pressure-sensitive adhesive layer containing one or more medicament capable of being transdermally absorbed or delivered onto the skin surface over the plurality of heat generating conductive fibers and the substrate, wherein the heat generating conductive fibers are substantially embedded within the pressure sensitive adhesive layer; and
electrically connecting a source of electrical energy to the conductive fibers, adding to the pressure-sensitive adhesive.

37. A skin-contacting heatable dressing comprising:
a pressure-sensitive adhesive layer having a first skin-contacting side and a second side;
heat generating conductive fibers substantially embedded within the skin-contacting pressure sensitive adhesive layer; and
a source of electrical energy electrically connected to the conductive fibers, wherein the source of electrical energy is a thin film battery and the thin film battery (a) forms at least a portion of a backing layer on the second side of the dressing, (b) is contained within a backing layer on the second side of the dressing, (c) is in a separate layer between a backing layer on the second side of the dressing and the pressure-sensitive adhesive layer, or (d) is in a separate layer over a backing layer on the second side of the dressing.

38. A skin-contacting heatable dressing comprising:
a pressure-sensitive adhesive layer having a first skin-contacting side and a second side and lateral edges;
heat generating conductive fibers substantially embedded within the skin-contacting pressure sensitive adhesive layer;
a source of electrical energy electrically connected to the conductive fibers;
conductive electrical leads in the pressure-sensitive adhesive layer providing electrical connection between the source of electrical energy and the conductive fibers, wherein the conductive electrical leads are disposed along each of two opposite lateral edges with the conductive fibers providing electrical connection between the electrical leads.

39. A skin-contacting heatable dressing comprising:
a pressure-sensitive adhesive layer having a first skin-contacting side and a second side and first and second longitudinally extending lateral edges on opposite sides of the adhesive layer;
first and second conductive electrical leads extending along the respective first and second lateral edges;
heat generating conductive fibers substantially embedded within the skin-contacting pressure sensitive adhesive layer and extending across the adhesive layer from the first conductive electrical lead to the second conductive electrical lead, the conductive electrical leads being in electrical contact with at least a portion of the conductive fibers; a backing layer on the second side of the pressure-sensitive adhesive layer; and
a source of electrical energy electrically connected to the conductive fibers via the first and second conductive electrical leads, wherein the source of electrical energy comprises a thin film battery.

* * * * *

UNITED STATES PATENT AND TRADEMARK OFFICE
CERTIFICATE OF CORRECTION

| | | |
|---|---|---|
| PATENT NO. | : 7,238,196 B2 | Page 1 of 1 |
| APPLICATION NO. | : 10/974358 | |
| DATED | : July 3, 2007 | |
| INVENTOR(S) | : Anne Marie Paule Wibaux | |

It is certified that error appears in the above-identified patent and that said Letters Patent is hereby corrected as shown below:

Column 29, line 42, replace "alone" with --along--.

Signed and Sealed this

Twenty-first Day of August, 2007

JON W. DUDAS
*Director of the United States Patent and Trademark Office*